United States Patent [19]
Steinhaus et al.

[11] Patent Number: 5,188,117
[45] Date of Patent: Feb. 23, 1993

[54] NOTCH FILTER NOISE REJECTION SYSTEM IN A CARDIAC CONTROL DEVICE

[75] Inventors: Bruce M. Steinhaus, Parker; Richard M. T. Lu, Highlands Ranch, both of Colo.

[73] Assignee: Telectronics Pacing Systems, Inc., Englewood, Colo.

[21] Appl. No.: 782,586

[22] Filed: Oct. 25, 1991

[51] Int. Cl.$^5$ .............................................. A61B 5/0456
[52] U.S. Cl. ..................................................... 128/708
[58] Field of Search ............................... 128/702–706, 128/708

[56] References Cited

U.S. PATENT DOCUMENTS

| | | | |
|---|---|---|---|
| 4,296,755 | 10/1981 | Judell | 128/705 |
| 4,436,093 | 3/1984 | Belt | 128/419 PG |
| 4,516,579 | 5/1985 | Imich | 128/419 PG |
| 4,557,266 | 12/1985 | Schober | 128/702 |
| 4,616,659 | 10/1986 | Prezas et al. | 128/708 |
| 4,649,931 | 3/1987 | Beck | 128/708 |
| 4,692,719 | 9/1987 | Whigham | 332/11 D |
| 4,708,144 | 11/1987 | Hamilton et al. | 128/708 |
| 4,754,762 | 7/1988 | Stuchl | 128/704 |
| 4,779,617 | 10/1988 | Whigham | 128/419 P |
| 4,821,724 | 4/1989 | Whigham et al. | 128/419 P |
| 5,048,535 | 9/1991 | Maruyama | 128/708 |

OTHER PUBLICATIONS

Holsinger et al., "IEEE Transactions on Biomedical Engineering", vol. BME 18, No. 3 May 1971, pp. 212–217.

Primary Examiner—William E. Kamm
Attorney, Agent, or Firm—Gottlieb, Rackman & Reisman

[57] ABSTRACT

A physiological event signal sensing system in a cardiac control or monitoring device for detecting spontaneous cardiac electrical events which may be obscured by continuous or burst EMI line frequency noise. The noise rejecting sensing system of this invention senses and samples cardiac signals which may include a noise component which is produced by power line interference in addition to a physiological signal component. The sampling frequency is selected to be an integer multiple of at least one common power line frequency. The system notch filters the cardiac signal to remove line frequency components, using either or both lowpass and highpass notch filtering coefficients, then limits the filtered output to the amplitude of the corresponding filter input to remove filter output signals caused by the sudden termination of line frequency noise which is characteristic of burst noise.

28 Claims, 11 Drawing Sheets

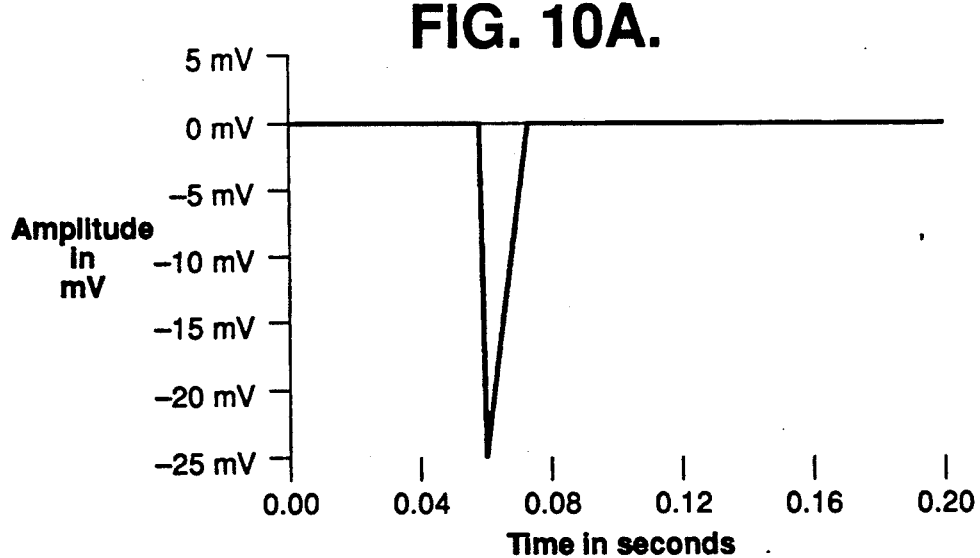
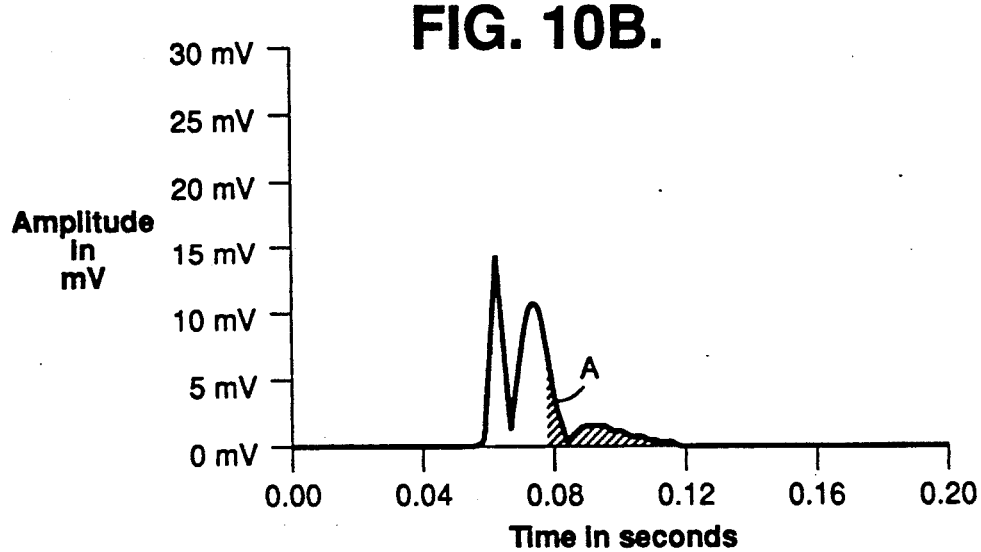
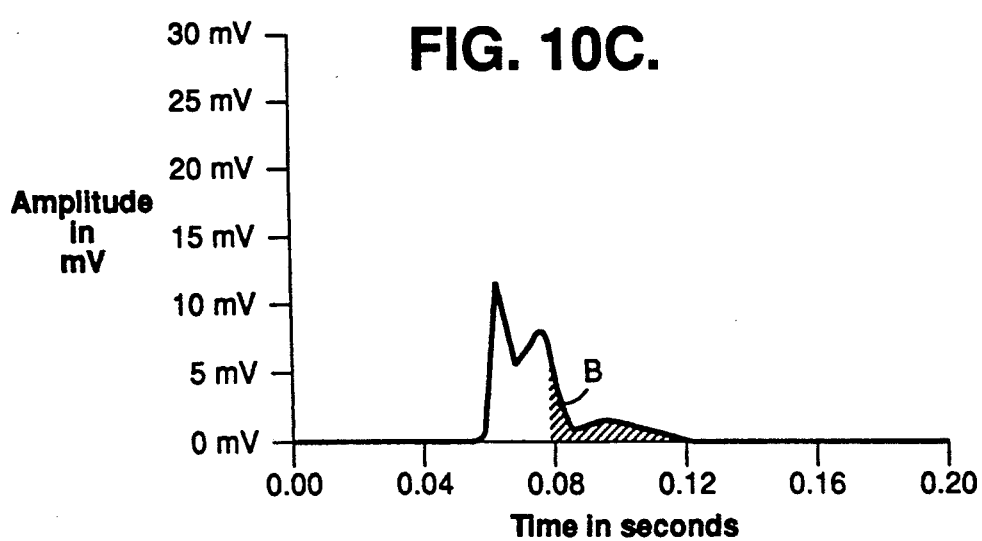

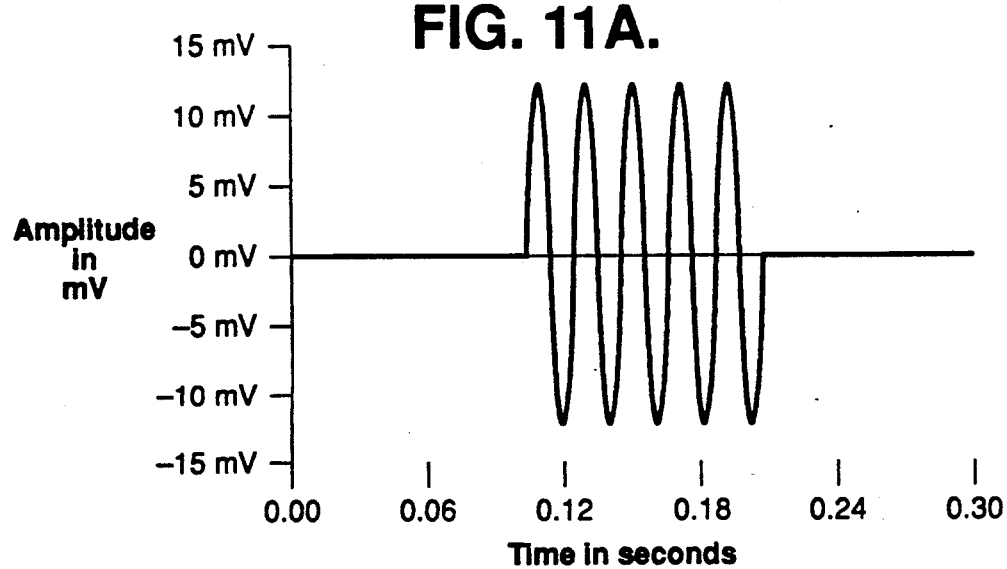
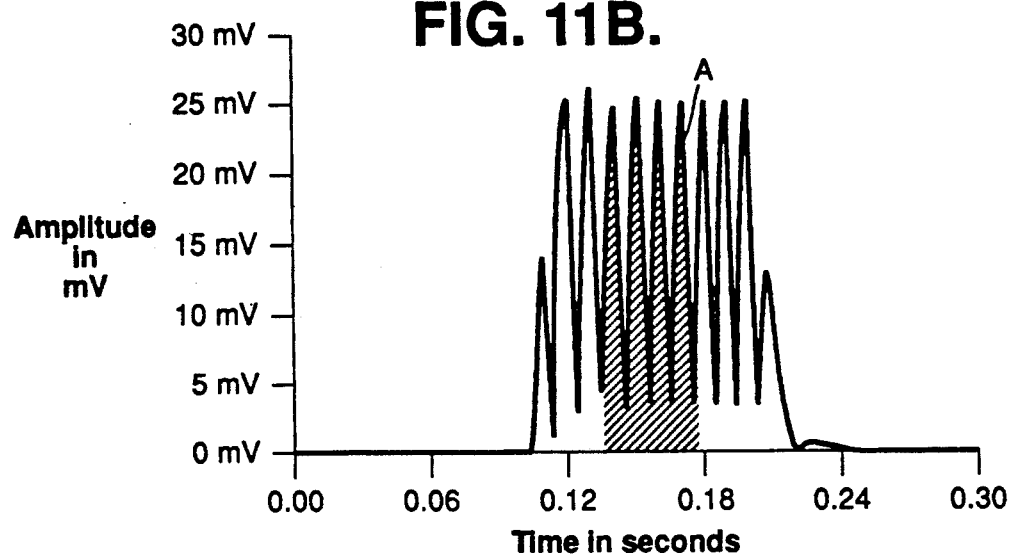
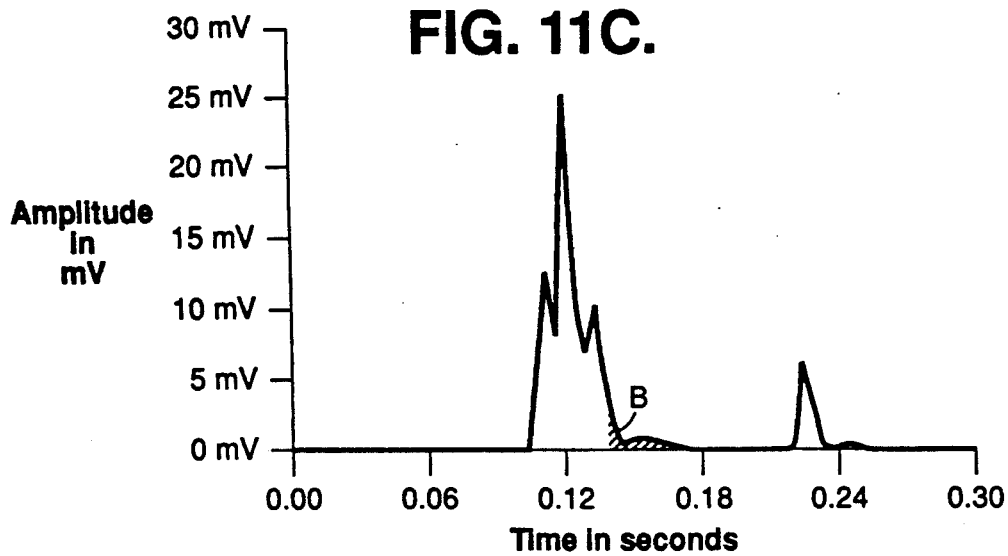

NOTCH FILTER NOISE REJECTION SYSTEM IN A CARDIAC CONTROL DEVICE

TECHNICAL FIELD

This invention relates generally to cardiac control and monitoring devices including implantable pacemakers, arrhythmia control systems and defibrillators and external Holter monitors, and more particularly to systems within such devices for improving line frequency noise rejection capabilities and increasing noise immunity while meeting low-power constraints.

BACKGROUND OF THE INVENTION

A typical modern-day cardiac control device maintains the capability to sense cardiac electrical activity as well as a capability to deliver an electrical or pharmaceutical therapy. Although the present invention has application to any cardiac control device sensing channel in which noise is to be rejected, the invention can be understood most readily by considering a simple ventricular demand VVI pacemaker (ventricular pacing and sensing; inhibited mode). Typically, demand VVI pacemakers generate a stimulation pulse after a preset time interval in the absence of the sensing of a heart's spontaneous beat within a predetermined interval. If the pacemaker senses a spontaneous beat, it does not generate a stimulation pulse. Following either a stimulated (paced) or spontaneous heartbeat, the pacemaker presets the cycle interval timer and enters a new sensing interval, usually following an initial time period during which pacing is disabled. The pacemaker continuously repeats the cardiac cycle of operations. The demand VVI pacemaker employs electrodes which are implanted within the right ventricle of the heart both for delivering the stimulus and for sensing spontaneous heartbeats.

Noise in the sensing channel can lead to erroneous operation. In the worst case, the pacemaker may interpret continuous noise as representing rhythmic heartbeats and fail to generate pacing stimuli even when the heart is not beating properly. To prevent this occurrence, pacemakers are often designed to automatically convert from a VVI demand mode to a VOO fixed rate (ventricular pacing at fixed rate; no sensing) mode of operation upon the detection of noise which prevents the reliable sensing of spontaneous heartbeats. The automatic mode switch, which may be termed "noise reversion pacing", is disadvantageous because it prevents the heart from beating at a natural rhythm and increases power drain on the battery due to the possible generation of continuous, unnecessary stimulation pulses.

A pacemaker detects noise by defining a refractory sensing interval, during which sensed electrical events are classified as noise. Pacemakers are designed to provide absolute and relative refractory intervals. The absolute refractory period (ARP) is a fixed interval which immediately follows a stimulated or spontaneous heartbeat. During the ARP, sensing is totally disabled to allow the afterpotential from a stimulus and the heart's evoked response to dissipate. The relative refractory period (RRP), which immediately follows the ARP, is provided to allow detection of noise. During the RRP, the after-potential from the stimulus has dissipated and cardiac signals are quiescent, therefore noise detection is possible. Cardiac events should not occur during the RRP because it occurs too soon after a heartbeat. Therefore, the pacemaker classifies sensed events during the RRP as noise and restarts the RRP timer. As long as the RRP is in progress, sensed events verify that noise is present, causing the pacemaker to restart the RRP timer and, therefore, delaying sensing for the purpose of inhibiting stimulation pulse generation. If the pacemaker continually restarts the RRP through the time that a pacing stimulus is due, it will switch to noise reversion pacing and generate the pacing stimulus, as stated previously.

Other types of cardiac control devices, which are not pacemakers, sense noise in a different manner but may respond in a similar manner. For example, antitachycardia pacemakers and defibrillators may define a noise window at some interval following a pacing stimulus or spontaneous heartbeat (e.g., about 50 to 100 msec post-event). When the device senses events in the noise window in a particular preponderance of cardiac cycles (e.g., 15 of 16, or 7 of 10), it will initiate VOO pacing. Inherent in this response to noise sensing are the drawbacks of noise reversion pacing (i.e., preventing the heart from beating at a natural rhythm and elevated power drain). In addition, these sensing methods may fail to distinguish noise from fibrillation. A VOO pacing response to fibrillation is woefully inadequate. Since antitachycardia pacemakers and defibrillators are intended for usage in heart patients who are at risk of arrhythmia episodes, it is critical that such a device can distinguish fibrillation from noise.

Noise rejection systems in the prior art have generally involved the making of adjustments to the pacemaker sensitivity. (For example, see U.S. Pat. No. 4,516,579, invented by Irnich and entitled "Interference Recognition Circuit in a Heart Pacemaker", issued May 14, 1985.) Sensitivity refers to the magnitude of an input signal which is sufficient to cause the pacemaker to sense a cardiac event. The act of lowering the sensitivity reduces the effect of noise by requiring a higher input signal level to exceed the threshold. These noise rejection systems are effective only in response to continuous noise. Whigham, in U.S. Pat. No. 4,779,617, entitled "Pacemaker Noise Rejection System", issued Oct. 25, 1988, discloses a noise rejection system which is designed to reduce electrophysiological noise, such as noise arising from a patient's skeletal muscles. This noise rejection system also operates by adjusting the pacemaker's sensitivity setting.

Other prior art devices reduce the influence of noise on a pacemaker system by filtering the data stream that enters into the sensing circuit, rather than adjusting sensitivity. Belt, in U.S. Pat. No. 4,436,093, entitled "Cardiac Pacer Having Active Notch Filter System", issued Mar. 13, 1984, discloses a noise rejection system which filters the electrical signal sensed within the heart to reduce continuous line frequency noise. However, this system does not improve noise immunity to skeletal muscle noise or bursts of line frequency noise.

Other filtering techniques, including fixed and adaptive digital methods, have been implemented to reduce the influence of line frequency noise. The overriding disadvantage of these methods, at least for applications in current implantable devices, is circuit or software complexity and a requirement for floating point computations.

Other less computationally-demanding methods involve morphology analysis. One example is an improved QRS detection method in which a device senses the amplitude of an electrical signal of the heart and counts the number of times the signal crosses a predetermined threshold value. A true sense occurs if the count number is within a preset range over a time interval of a particular duration. This method accurately detects QRS signals only if the threshold level is correctly set. Unfortunately, setting the threshold correctly is difficult due to large variations in the amplitude of QRS signals from patient to patient. Also, the accuracy of morphology detection techniques is limited due to potentially large beat-to-beat variability inherent in physiological systems.

A further problem afflicting present-day devices relates to the rejection of amplitude modulated or burst electromagnetic fields. One source of burst line frequency noise is faulty, or poorly designed, appliances where the patient is in contact with a line frequency AC powered device. The patient actually is part of an electrical pathway to ground. In contrast to sense detection in the presence of continuous additive line frequency interference, the operation of the sensing circuit during amplitude modulated or burst electromagnetic interference (EMI) is probably more important to patient safety. Burst line frequency noise is a potentially dangerous situation for pacemaker-dependent patients because burst noise may inhibit stimulus generation in a cardiac control device. The potential hazard of continuous line frequency noise, in comparison to burst noise, is less precarious because continuous line noise will cause the device to pace asynchronously with respect to a spontaneous cardiac rate, but the device will still support the patient.

All of the aforementioned noise rejection methods are intended to distinguish spontaneous cardiac events from noise arising from various sources. A supplementary objective, in the cardiac control system of the present invention, is noise reduction to permit a detailed analysis of electrophysiological signal waveforms.

A large physiological signal component exists at frequencies corresponding to worldwide line frequencies. For example, the frequency spectrum of intrinsic cardiac electrograms show significant power at frequencies right at, and around, 50 and 60 Hz. The general purpose highpass or lowpass filters of present-day cardiac control and monitoring devices are unable to filter out line noise without markedly attenuating physiologic signals. Hardware notch reject filters with sufficient Q to filter line frequencies but retain physiological signal components are inappropriate for an implantable system due to the requirement for additional circuit components and added current drain. Also, an integrated circuit capable of meeting the Q requirements would involve very difficult design and production problems arising from tight tolerances on the IC process to provide a filter notch at the specified frequency. Therefore, there does not exist an appropriate analog hardware filter solution to this problem for implantable applications.

Accordingly, it is the primary object of this invention to provide an improved physiological event signal sensing system for a cardiac medical device.

It is a further object of this invention to provide an improved physiological event signal sensing system that reliably senses natural cardiac events which are obscured by the presence of either continuous noise or pulsed noise in the signal sensing system.

Another object of the invention is a physiological event signal sensing system that provides improved detection of spontaneous cardiac events in the presence of bursts of power line frequency noise which occur either during or outside of the heart's refractory period.

A still further object of the invention is a physiological event signal sensing system that provides improved detection of natural cardiac events in the presence of continuous power line frequency noise, thus maintaining hemodynamic efficiency.

Yet another object of the invention is a physiological event signal sensing system that utilizes digital notch filtering and morphology analysis in providing improved detection of spontaneous cardiac events in the presence of bursts of power line frequency noise.

A further object of the invention is a physiological event signal sensing system that provides improved detection of natural cardiac events in the presence of noise in the signal sensing system, thus preventing asynchronous pacing (VOO or AOO mode pacing) when the heart is beating with a natural rhythm and conserving energy in an implantable system.

It is still another object of this invention to provide an improved physiological event signal sensing system that detects and logs information concerning steady state noise levels, and the occurrences of onset and offset of noise interference.

Further objects, features and advantages of this invention will become apparent as the following description proceeds.

SUMMARY OF THE INVENTION

Briefly stated, and in accordance with one embodiment of the invention, a physiological event signal sensing system in a cardiac medical device is provided. The system comprises: means for sensing a cardiac signal, which signal includes a physiological component and includes a noise component produced by power line interference; means for sampling the instantaneous amplitude values of the cardiac signal at a sampling frequency of Fs; means for combining the amplitude values for n consecutive samples to derive a notch filter output signal retaining the physiological component while attenuating the power line noise component, wherein n is preselected so that Fs/n defines the frequency of the power line noise component and wherein the amplitude values are combined according to a predetermined notch filter function; means for comparing the notch filter output signal with a predetermined threshold level; and, means responsive to the notch filter output signal exceeding the predetermined threshold level for determining the occurrence of a heartbeat.

In accordance with another aspect of the invention, a physiological event signal sensing system in a cardiac medical device is provided. The system comprises: means for sensing a cardiac signal, which signal includes a physiological component and includes a noise component produced by power line interference; means for sampling the instantaneous amplitude values of the cardiac signal at a sampling frequency of Fs; means for combining the amplitude values for n consecutive samples to derive a notch filter output signal retaining the physiological component while attenuating the power line noise component, wherein n is preselected so that Fs/n defines the frequency of the power line noise component and wherein the amplitude values are combined according to a predetermined notch filter function; rectifying means responsive to the sampling means for rectifying the sampled cardiac signal and responsive to the combining means for rectifying the notch filter output signal; means for comparing each of the rectified notch filter output signal samples to the corresponding time sample of the rectified samples cardiac signal; means responsive to the comparing means for setting each sample of the notch filter output signal to the smaller value; means for comparing the minimized notch filter output signal with a predetermined threshold level; and means responsive to the notch filter output signal exceeding the predetermined threshold level for determining the occurrence of a heartbeat.

In accordance with a still further aspect of the invention, a physiological event signal sensing system in a cardiac medical device in provided. The system comprises: means for sensing a cardiac signal which signal includes a physiological component and includes a noise component produced by power line interference; means for sampling the instantaneous amplitude values of the cardiac signal at a sampling frequency of Fs; means for combining the amplitude values for n consecutive samples to derive a notch filter output signal retaining the physiological component while attenuating the power line noise component, wherein n is preselected so that Fs/n defines the frequency of the power line noise component and wherein the amplitude values are combined according to a predetermined notch filter function; integrating means responsive to the sampling means for integrating the sampled cardiac signal and responsive to the combining means for integrating the notch filter output signal; means for determining the ratio of the integrated notch filter output signal to the integrated sampled cardiac signal; means for comparing the ratio with a predetermined threshold level; and, means responsive to the notch filter output signal exceeding the threshold level for determining the occurrence of a heartbeat.

In accordance with another aspect of the invention, a method of operating a physiological event signal sensing system in a cardiac medical device is provided. The method comprises the steps of: sensing a cardiac signal, which signal includes a physiological component and includes a noise component which is produced by power line interference; sampling the instantaneous amplitude values of the cardiac signal at a sampling frequency of Fs; combining the amplitude values for n consecutive samples to derive a notch filter output signal retaining the physiological component while attenuating the power line noise component, wherein n is preselected so that Fs/n defines the frequency of the power line noise component and wherein the amplitude values are combined according to a predetermined notch filter function; comparing the notch filter output signal with a predetermined threshold level; and determining the occurrence of a heartbeat when the notch filter output signal exceeds a predetermined threshold level.

In accordance with a still further aspect of the invention, a method of operating a physiological event signal sensing system in a cardiac medical device is provided. The method comprises the steps of: sensing a cardiac signal, which signal includes a physiological component and includes a noise component which is produced by power line interference; sampling the instantaneous amplitude values of the cardiac signal at a sampling frequency of Fs; combining the amplitude values for n consecutive samples to derive a notch filter output signal retaining the physiological component while attenuating the power line noise component, wherein n is preselected so that Fs/n defines the frequency of the power line noise component and wherein the amplitude values are combined according to a predetermined notch filter function; rectifying the sampled cardiac signal; rectifying the notch filter output signal; comparing each of the rectified notch filter output signal samples to the corresponding time sample of the rectified sampled cardiac signal; setting each sample of the notch filter output signal to the smaller value resulting from the comparing step; comparing the minimized notch filter output signal with a predetermined threshold level; and determining the occurrence of a heartbeat when the minimized notch filter output signal exceeds a predetermined threshold level.

BRIEF DESCRIPTION OF THE DRAWINGS

While the specification concludes with claims particularly pointing out and distinctly claiming the subject matter regarded as the invention herein, it is believed that the present invention will be more readily understood from the following description, taken in conjunction with the accompanying drawings, in which:

FIGS. 10A, 10B, and 10C are sample illustrations of a simulated cardiac signal waveform (FIG. 10A) and processed signals at different stages of analysis as performed by the noise rejection system of the present invention, including the cardiac signal waveform after processing by a typical cardiac pacemaker sensing circuit (FIG. 10B), and the cardiac signal waveform after processing by a dual frequency lowpass filter and after minimization of the output of the filter to the value of the input to the filter (FIG. 10C); and FIGS. 11A, 11B, and 11C are sample illustrations of a burst line frequency noise waveform (FIG. 11A) and processed signals at different stages of analysis as performed by the noise rejection system of the present invention, including the burst line frequency noise waveform after processing by a typical cardiac pacemaker sensing circuit (FIG. 11B), and the noise waveform after processing by a dual frequency lowpass filter and after minimization of the output of the filter to the value of the input to the filter (FIG. 11C).

DETAILED DESCRIPTION

Figure 1:
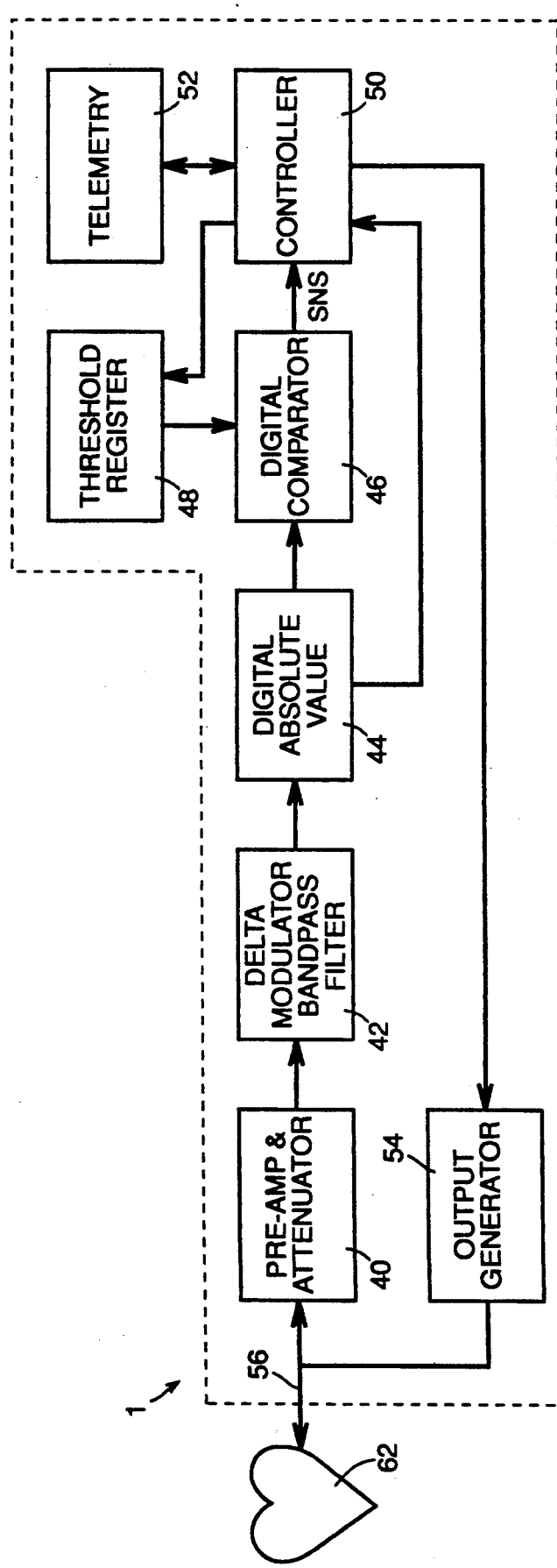
FIG. 1 is a block diagram of a cardiac control device in the form of an implantable cardiac pacemaker in which the system of the invention may be incorporated.

Referring to FIG. 1, there is depicted a block diagram of a cardiac control system in the form of a cardiac pacemaker, shown generally at 1. Although the preferred embodiment of the invention, a noise rejection system, is described as comprising one part of a cardiac pacemaker, it is to be understood that the invention is intended for usage in general in any cardiac control and monitoring device which senses cardiac electrical signals. Such devices may include defibrillators, antitachycardia pacemakers, electrical sensing drug infusion pumps, and internal and external cardiac monitors and electrophysiology recorders.

Pacemaker 1 is designed to be implantable in a patient and includes an output generator 54, which is controlled by commands from controller 50, and appropriate leads 56 for electrically connecting the output generator 54 to a patient's heart 62. The leads 56 also connect the patient's heart to sensing circuitry, beginning with a preamplifier and attenuator circuit 40, the attenuator of which is variable. If the pacemaker 1 is a dual chamber device, leads 56 will generally include an atrial cardiac lead pair extending to the atrium of the patient's heart for sensing of atrial cardiac electrical activity and for the administration of pacing therapy to the atrium, and a ventricular cardiac lead pair extending to the ventricle of the patient's heart for sensing of ventricular cardiac electrical activity and for the administration of pacing therapy to the ventricle. In a single chamber device, leads will generally include a lead pair to only one of the heart chambers. Commands from controller 50 to output generator 54 determine which cardiac chamber is stimulated and regulate the timing, amplitude, duration, and stimulus pulse waveform of the delivered pacing therapy.

The preamplifier and attenuator circuit 40 amplifies the electrical signal from the heart by a gain of 30 in the preferred embodiment of the invention. An eight bit control signal from the controller 50 sets the variable attenuator in circuit 40 to a setting between 0 and 255/256 to attenuate or scale the input signal. A change in the attenuator setting affects the voltage deviation required at the sensing electrode for a sense to be registered. A delta modulator and bandpass filter circuit 42 receives analog signals from preamplifier and attenuator circuit 40, filters the incoming data, and converts it to digital form. A preamplifier and attenuator circuit and a delta modulator and bandpass filter circuit which are suitable for a device which incorporates the noise rejection system of the present invention is described in three patents by Whigham, U.S. Pat. No. 4,692,719, entitled "Combined Pacemaker Delta Modulator and Bandpass Filter" and issued Sep. 8, 1987, U.S. Pat. No. 4,779,617, entitled "Pacemaker Noise Rejection System" and issued Oct. 25, 1988, and U.S. Pat. No. 4,821,724, entitled "Pacing Pulse Compensation" and issued Apr. 18, 1989.

Figure 2:
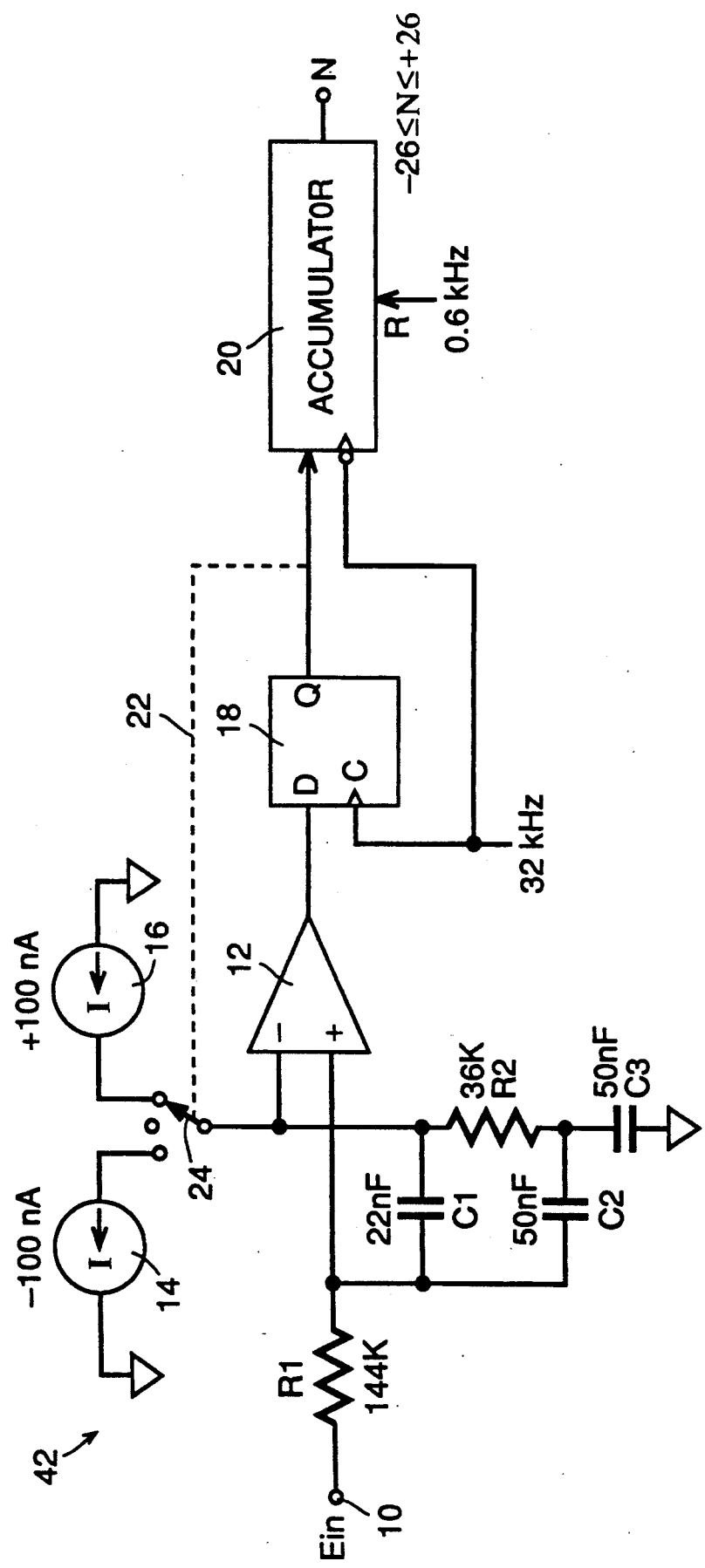
FIG. 2 is a schematic block diagram of a combined delta modulator and bandpass filter circuit which is one of the elements of FIG. 1.

FIG. 2 represents a more detailed diagram of the combined delta modulator and bandpass filter circuit 42 which operates on a pacemaker sense input signal, Ein, from the preamplifier and attenuator circuit 40 of FIG. 1. In FIG. 2, Ein is applied to terminal 10 and passes through a resistor R1 to the plus input of a differential amplifier 12. The output of the differential amplifier is applied to the D input of a flip-flop 18, which is clocked at a 32 kHz rate. The Q output of the flip-flop 18 reflects the state of the input at the preceding clock pulse. A dashed line 22 represents the flip-flop's control over switch 24, which is shown in the position in which it is maintained when the Q output of the flip-flop is high. A 100nA current source 16 is electrically interconnected with the circuit when the position of the switch 24 is as shown. Alternatively, for the opposite state of the flip-flop 18, the switch 24 interconnects a 100nA current source 14, which has the opposite polarity of current source 16, into the circuit. The switch 24 may also take an intermediate position, which interconnects neither current source to the circuit. When current does flow, it flows through three capacitors C1, C2 and C3. Capacitor C1 is of one magnitude and capacitors C2 and C3 are each of another magnitude, as shown. The capacitor C1 and resistors R1 and R2, in combination with the differential amplifier 12, perform bandpass filtering of the pacemaker sense signal. This circuit performs delta modulation and bandpass filtering using a single amplifier, thereby requiring less power to operate the pacemaker.

By virtue of control by line 22, which determines the position of switch 24, the circuit operates as a delta modulator in response to changes in the input signal, Ein. For example, when Ein changes such that the minus input potential to differential amplifier 12 begins to decrease from a quiescent level, the amplifier output goes high. The next 32 kHz clock pulse, applied to the C input of flip-flop 18, causes the Q output of the flip-flop to go high, causing current to flow from the current source 16 through capacitor C1. As a consequence, this restores the potential at the minus input of the differential amplifier 12 to the quiescent level. In a similar manner, when Ein changes to increase the potential at the minus input of the differential amplifier 12 and to bring the amplifier output low, the flip-flop 18 resets. This causes control line 22 to move switch 24 and connect the circuit with current source 14, driving the current through C1 in the opposite direction and reducing the potential at the minus input of the differential amplifier 12 to the quiescent level. Accordingly, the output of the differential amplifier 12 serves the dual purposes of controlling the switch to the current sources and representing a bit sample indicative of the manner in which the input signal is changing.

The differential amplifier minus input is a virtual ground. Capacitor C1 is charged and discharged by the current sources 16 and 14 so that the potential at the input is increased or decreased by a capacitor potential to create a result in which the potential at the minus input to the amplifier is equal to a reference potential at the plus input. In a quiescent condition, the flip-flop output is alternating 0 and 1 bit samples. A change in the potential at the input causes the flip-flop output to convert to a number of bit samples of the same value until the capacitor charges or discharges to an extent which compensates for the change at the input. In this manner, the number of bit samples of constant value at the output of the delta modulator represents the magnitude of the change in the input signal. The value of the output bits depicts the direction of the change.

The output of flip-flop 18, a sequence of bit values expressing changes in the input signal over time, is applied to the data input of an accumulator 20, which is also clocked at the 32 kHz rate (actually 32768 Hz), but on alternate phases. During each clock cycle, after the flip-flop state is established, the accumulator count N increments or decrements according to the state of the flip-flop. The accumulator resets, as shown at R, at a 0.6 kHz rate (actually 595.78 Hz corresponding to 1.68 millisecond intervals). During each 1.68 millisecond accumulator cycle, there are 55 clock pulses. The flip-flop is clocked for 53 of these clock pulse cycles to delta modulate the input signal. In the remaining two clock pulse cycles, the flip-flop is not clocked, the switch 24 connects neither current source to the circuit, and the circuit performs "housekeeping" functions such as loading a register from the accumulator, resetting the accumulator, and balancing the current sources. When the accumulator is reset, it takes the count N value of −26. Therefore, every 1.67 milliseconds the accumulator provides a sum of the string of 52 zero and one bits to produce a number between, and including, the limits of −26 and +26. The controller 50 of FIG. 1 preferably reads this output every other 0.6 kHz cycle to provide a sampling frequency of 300 Hz.

Again referring to FIG. 1, the digital data signal from the delta modulator and bandpass filter circuit 42 progresses to a digital absolute value circuit 44 and the controller 50. The digital absolute value circuit derives the absolute value of the digital data signal and delivers it to a digital comparator 46. The digital data signal passes to the controller 50 without absolute value rectification to preserve signal polarity information for further processing.

The controller 50 presets a threshold value into a threshold register 48 which the digital comparator 46 compares with the absolute signal value from block 44. If the absolute signal value is greater than the threshold, the digital comparator generates a sense wakeup signal (SNS) to notify the controller 50 of such an event. Note that in a dual chamber device the signal SNS includes signals (not shown) for both the atrium (ASNS) and the ventricle (VSNS).

Telemetry circuit 52 provides a bidirectional link between the controller 50 of pacemaker 1 and an external device such as a programmer. It allows data such as the operating parameters to be read from or altered.

The controller 50, which may be a microprocessor, controls all operations of the pacemaker 1. In the preferred embodiment of the present invention, the noise rejection system is a software routine performed by the controller 50. It is to be understood that the invention is not limited to a software implementation but may also be embodied in other forms including analog and/or digital electronic circuits.

More particularly, the controller 50 writes command signals to the output generator 54 to determine the heart chamber to be stimulated and to set the stimulating pulse timing, amplitude, duration, and morphology. For example, the controller 50 sets the pulse delivery parameters for the purpose of charge balancing a stimulus output. The controller 50 sets the sensing sensitivity and threshold by writing attenuator settings to the preamplifier and attenuator circuit 40, and writing threshold settings to the threshold register 48. In a dual chamber device, there are separate attenuator and threshold settings for each heart chamber. The controller receives sensed signals from the delta modulator and bandpass filter 42 and governs the timing and number of intracardiac electrogram samples employed. In addition, it determines and executes any signal filtering required for signal analysis. As the controller 50 performs signal sampling, it carries out the analysis necessary for the diagnostic purposes of the pacemaker, as described below.

Figure 3:
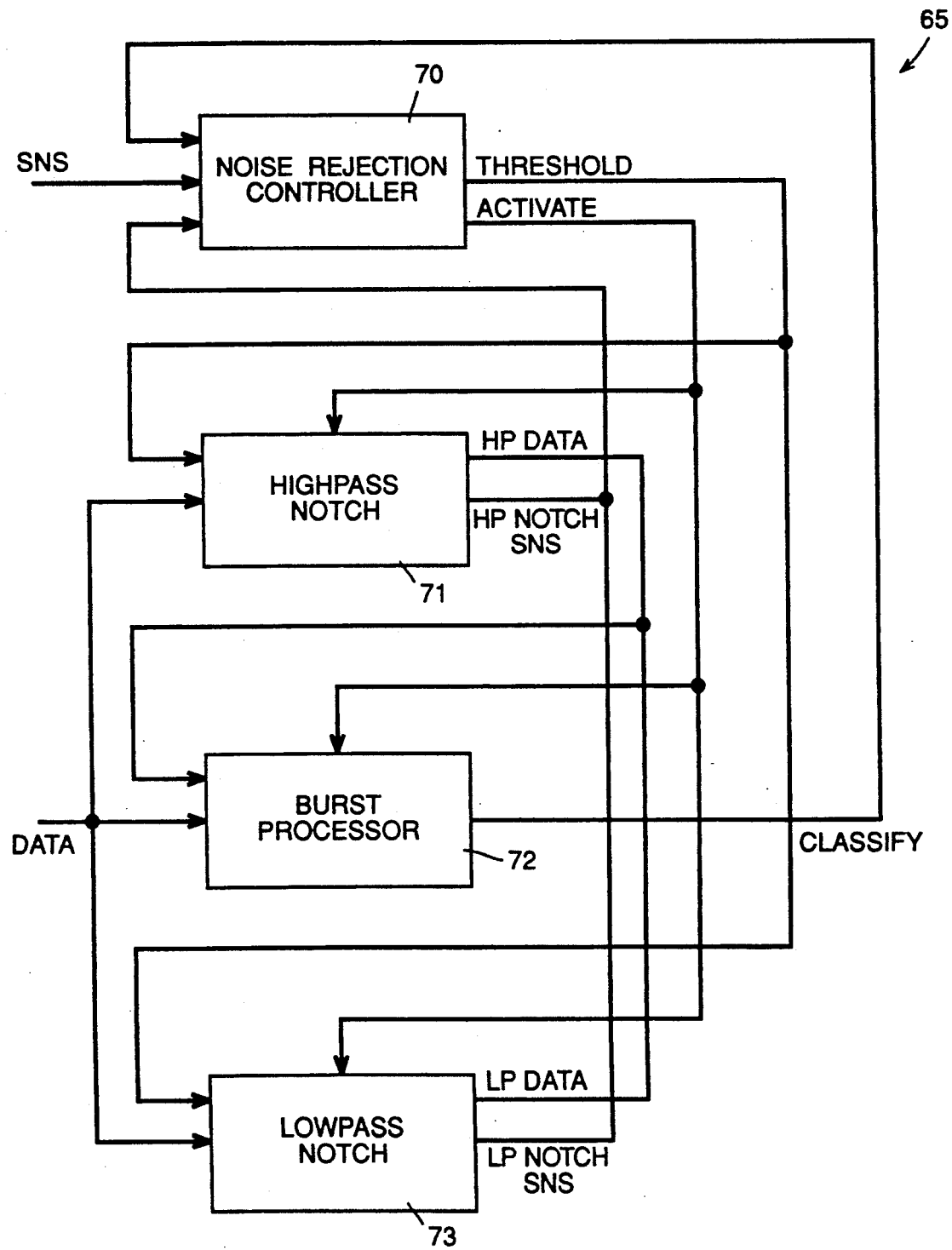
FIG. 3 is a block diagrammatic representation of the illustrative embodiment of the invention.

FIG. 3 is a block diagram representation of the noise rejection system of the present invention, shown generally at 65. A particular cardiac control or monitoring device may include one or more noise rejection systems according to the intended function to be performed by the device. For example, a dual chamber pacemaker device may include two noise rejection systems, one for the atrium and one for the ventricle. In the preferred embodiment of the invention, each block symbolizes a software routine which is performed by the controller 50 of FIG. 1. A software implementation is preferred over electronic circuit implementations because of the flexibility offered by software control in a system which performs high and lowpass filtering operations, signal processing, and signal morphology analysis to achieve the objectives of multiple cardiac control and monitoring devices. Ultimately, in a particular device with precise functional specifications, an electronic circuit embodiment of the invention may be preferred due to energy consumption constraints. The integer addition and subtraction operations which are employed to perform highpass and lowpass notch filtering methods are necessary elements in either a software or a hardware implementation.

Referring to FIG. 3, a noise rejection controller 70 governs the operations of all filtering and processing blocks of the noise rejection system by means of ACTIVATE signals which enable a highpass notch filter 71, a lowpass notch filter 73, and a burst processor 72. The noise rejection controller 70 may continuously enable one or more of these blocks. Alternatively, the noise rejection controller 70 may conserve energy by activating each block only when necessary. For example, the noise rejection system may normally remain in a quiescent state until activated by a sense detect signal, SNS, from the digital comparator 46 of FIG. 1. After completing a preselected set of operations, the noise rejection controller may return the system to an inactive state.

The notch filtering noise rejection system 65 of FIG. 3 distinguishes between electrical line frequency noise, including burst electromagnetic interference and continuous line frequency noise, and spontaneous cardiac electrical signals. The input to this system is DATA which is sampled by the delta modulator and bandpass filter 42 of FIG. 1. In this description of the preferred embodiment of the invention, DATA is a cardiac electrical signal in the form of intracardiac electrograms. Other applications of noise rejection system 65 include nonimplanted medical devices in which the DATA signal may be cardiac electrical signals from surface electrocardiograms. DATA are samples of the instantaneous amplitude of cardiac signals which are digitized at a sampling frequency which is approximately an integer multiple of at least one power line frequency signal. In the preferred embodiment of the invention, the sampling frequency is 600 Hz, which is ten times the 60 Hz line frequency and twelve times the 50 Hz line frequency. The sampled data sequence may be considered to be split into two flow paths.

In a first data path, DATA is processed directly through the burst processor 72. In this instance, the noise rejection system 65 processes an unfiltered representation of the input signal DATA by replacing each signal amplitude sample with its absolute value and then integrating the sequence of absolute value samples for a predetermined length of time.

In a second data path, data is processed by the burst processor 72 only after previously filtering DATA through the highpass notch filter 71 or the low pass notch filter 73. Under the regulation of noise rejection controller 70, the noise rejection system filters interference noise from the input data using digital notch filtering techniques. The noise rejection controller 70 determines which line frequency signal component is removed by selecting different digital filter coefficients. Each digital filter is characterized by a predetermined set of filter coefficients and produces a notch filtered output signal. The burst processor 72 then processes each filtered sequence of the second data path in the same manner as described above in connection with the first data path, (i.e., by replacing each negative sample with its absolute value and integrating the sequence). If the noise rejection controller 70 selects filtering of multiple line frequencies (for example, 50 Hz and 60 Hz), the burst processor 72 compares time-corresponding filtered samples for each line frequency and sets each time-corresponding sample to the smaller of the absolute values associated with each filter. The second data path may include multiple sub-paths, one for each digital notch filter (highpass 71 and lowpass 73) which is applied to the signal. In this manner, the second data path may include all combinations of highpass and lowpass filtering and filtering of 50 Hz and 60 Hz line frequencies.

Next the burst processor 72 compares the filtered data integral to the input data integral and classifies the input signal as line frequency noise when the input data integral is larger than a predetermined percentage of the filtered data integral. Otherwise, if the input signal is not classified as line frequency noise and the filtered data integral is larger than a predetermined multiplicative factor of the input data integral, the input signal is classified as a sensed cardiac event, such as a P wave (atrium) or an R wave (ventricle) depending on the location of sensing electrodes.

Within the second data path, the noise rejection controller 70 may activate lowpass digital notch filtering, which the lowpass notch filter performs, by integrating (summing) a sequence of DATA samples. A notch filter reduces signal components at a particular frequency, and at harmonically related frequencies, by virtue of a filter "zero" which occurs at the frequency which corresponds to the interval over which an integration operation occurs. In other words, by summing samples at regular intervals for the number of samples which corresponds exactly to one complete cycle of the rejection sample period, the amplitude contributed by the notch frequency is zero. This occurs whenever the sampling frequency is an integer multiple of the notch frequency. For example, a running sum of exactly 10 samples rejects 60 Hz frequencies, assuming a sample rate of 600 Hz. Likewise, a running sum of 12 samples rejects a 50 Hz component at that sample rate. A digital notch filter of this form is computationally efficient because it uses integer addition rather than floating point addition. Floating point calculations impose a high computational burden.

The highpass notch filter 71 performs highpass digital notch filtering by differentiation (subtracting of serial samples) of a sequence of a DATA string. Like a low pass notch filter, a highpass notch filter 71 reduces signal components at a particular frequency, and its related harmonic frequencies, by means of a filter "zero" which occurs at the frequency corresponding to the interval of differentiation. In other words, by subtracting two input samples that differ in time by an interval corresponding to the rejection sample period, the amplitude of the output sample resulting from signal components at the notch frequency is zero. This occurs, intrinsically, whenever the sampling frequency is an integer multiple of the notch frequency. At a sample rate of 600 Hz, rejection of 60 Hz occurs by subtracting, in a running manner, a sample exactly 10 sampling intervals prior to the current sample. Likewise, a running differential of 12 sampling intervals prior to the current sample rejects a 50 Hz component. A digital highpass notch filter of this form is computationally efficient because it utilizes integer valued subtraction.

Whether the noise rejection system incorporates either or both highpass and lowpass notch filters depends on the purposes and requirements of the cardiac control and monitoring device which embodies the system. In a noise rejection system used primarily to detect spontaneous cardiac events, highpass may be preferred over lowpass filtering because the highpass filter accentuates the steep slope of cardiac P or R waves, thereby offering an improved signal to noise ratio. In contrast, the lowpass notch filter inherently averages (smooths) the slope of the QRS complex, which diminishes the signal structure upon which event sensing is based.

If the noise rejection system is employed for the purpose of retaining the morphology of the cardiac signal while removing noise components, a lowpass notch filter is preferable since it removes noise while introducing less distortion than does the highpass filter. It may be desirable in a cardiac control or monitoring device to maintain high cardiac signal fidelity for the purpose of signal processing or analysis.

The noise rejection system of the invention addresses burst line frequency noise using digital notch filtering techniques in combination with additional signal processing to detect signal components arising from line frequency bursts and to distinguish these signal components arising from a physiological origin. The system extends the functionality of the sense detect circuitry of prior art cardiac pacemakers because it distinguishes between noise and true physiological sense signals in the signal giving rise to the sense detect.

Referring to FIGS. 1 and 3 together, upon activation, the highpass notch filter 71 processes a digital input signal from the delta modulator and bandpass filter circuit 42 of FIG. 1. The digital input signal is a sequence of samples occurring at a sampling frequency, Fs. The sample period, Ts, between these samples is 1/Fs. In the preferred embodiment of the invention, Fs is 600 Hz and Ts is 1.667 msec. The highpass notch filter 71 computes a running subtraction of the digital input signal sequence by subtracting one prior sample of the sequence, which occurred M samples previously, from the current input sample of the sequence, where M is the number of samples at frequency Fs which occur within the rejection notch sample period Trn of a rejection notch frequency Frn. For example, if sampling frequency Fs is 600 Hz and the rejection notch sample frequency Frn is 50 Hz, the rejection notch sample period is 20 msec (1/Frn), and, therefore, the number of samples, M, is 12 (Fs/Frn). Likewise, when sampling frequency Fs is 600 Hz and the rejection notch sample frequency Frn is 60 Hz, the rejection notch sample period is 16.67 msec, and, the number of samples, M, is 10. The following equation specifies the high-pass notch filtering operation:

$$Y_n = X_n - X_{n-M}$$

where x is the input signal to the highpass notch filter 71 (the output from the delta modulator and bandpass filter circuit 42 of FIG. 1), y is the filtered digital output (HP DATA) of the highpass notch filter, n is the current sample in the sequence, and M, as previously described, is the number of samples in the rejection notch period Trn. The highpass notch filter eliminates, with a zero DC gain, all additive signals, including line frequency noise, having frequencies either at line frequency or at an integer multiple thereof and as to which the sample frequency Fs is a harmonic frequency. This highpass notch filter also eliminates any DC component of additive noise.

Figure 4:
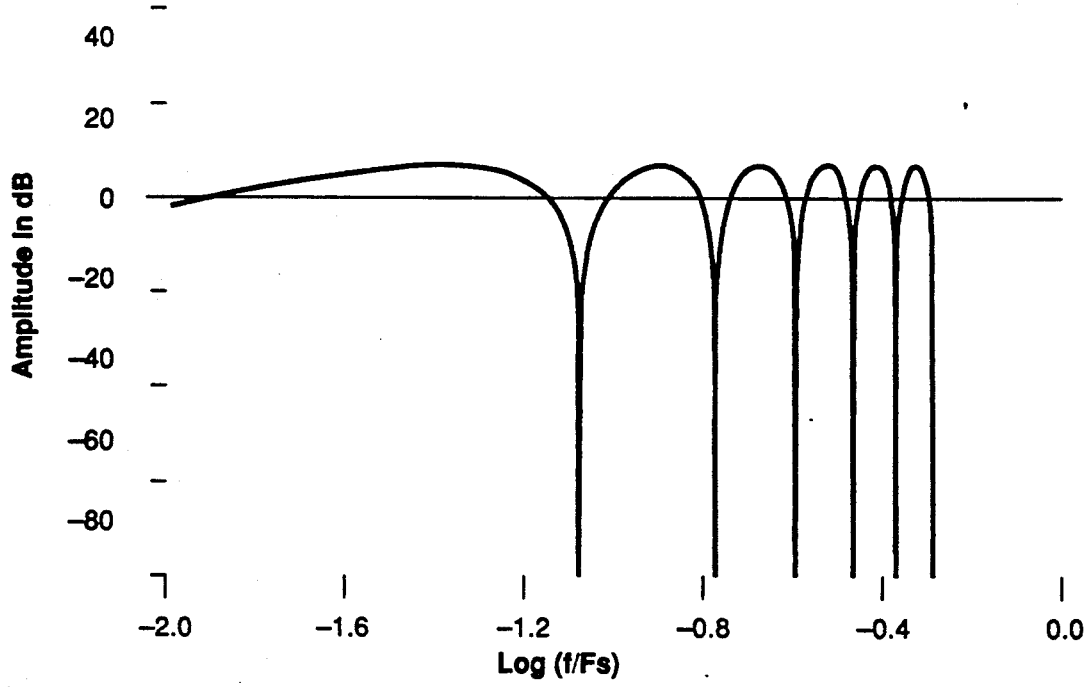
FIG. 4 is a graphical illustration of the bandpass characteristics of a highpass notch filter employed in the illustrative embodiment of the invention.

FIG. 4 illustrates the frequency response of a highpass notch filter 71. In this figure the ordinate scale represents signal amplitude in dB, and the abscissa scale represents the log to the base 10 of the signal frequencies, f, divided by the sampling frequency Fs (600 Hz in this case). As may be seen in the figure, significant attenuation of the signal occurs at points corresponding to 50 Hz and its harmonics.

A cardiac control or monitoring device may be implanted in a patient located within either a 50 Hz or 60 Hz line frequency environment. Also, such a patient may travel between such environments. It may therefore be beneficial to filter both 50 and 60 Hz line frequencies. To this end, the noise rejection controller 70 (FIG. 3) may configure the highpass notch filter 71 to apply notch filtering for both 50 and 60 Hz frequencies, compare the outputs y for each sample in the sequence, and select the minimum value for the overall output. Alternatively, the highpass notch filter 71 may perform notch filtering for both line frequencies, compare the output y to the previous output y for each line frequency, and select the output y corresponding to the minimum change from the previous sample for the final high-pass filter output. Note that the system may employ this method to eliminate more than two frequencies.

Figure 5:
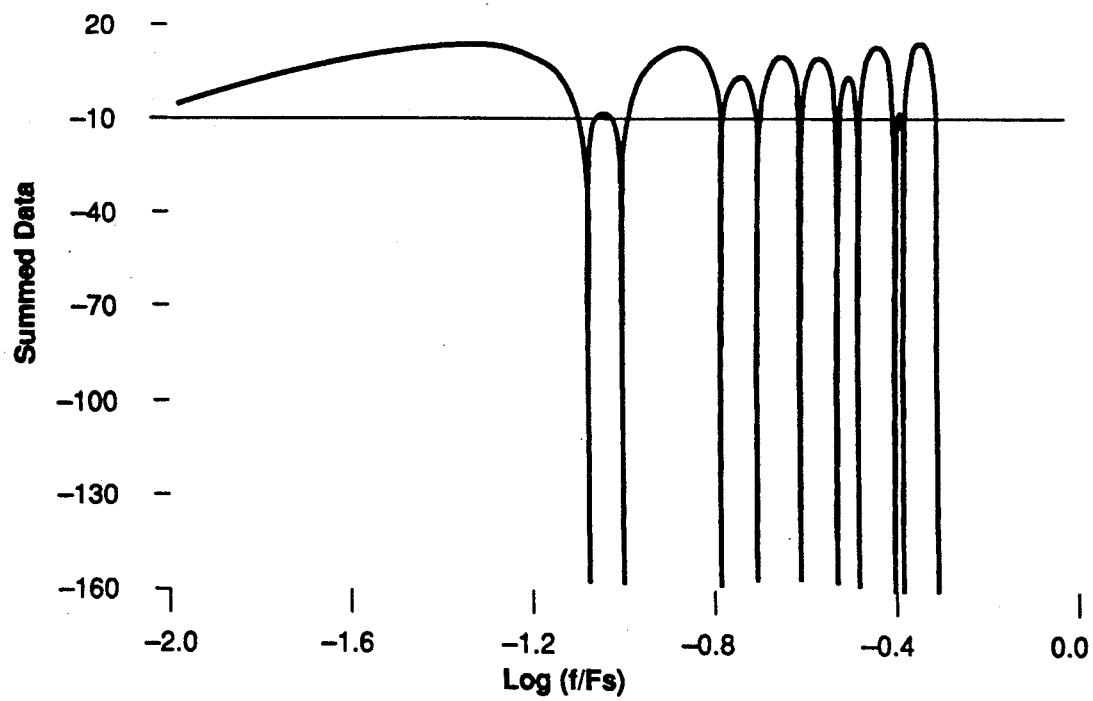
FIG. 5 is a graphical illustration of the bandpass characteristics of a dual frequency 50 Hz and 60 Hz highpass notch filter employed in the illustrative embodiment of the invention.

FIG. 5 illustrates the frequency response of a 50 Hz and 60 Hz dual frequency highpass notch filter. In this figure the ordinate scale represents signal amplitude in dB, and the abscissa scale represents the log to the base 10 of the signal frequencies, f, divided by a sampling frequency Fs of 600 Hz. As may be seen in the figure, significant attenuation of the signal occurs at points corresponding to 50 Hz and its harmonics, and also at points corresponding to 60 Hz and its harmonics.

Figure 6A:
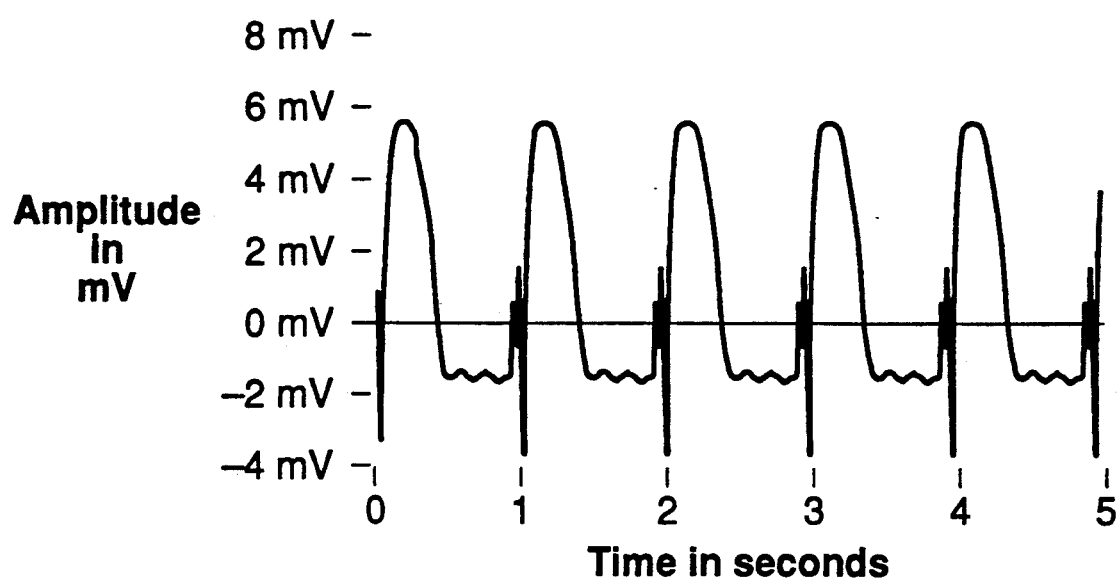
FIGS. 6A, 6B, 6C, and 6D are sample illustrations of cardiac signals at different stages of processing by the dual frequency highpass filter employed in the illustrative embodiment of the invention.
Figure 6B:
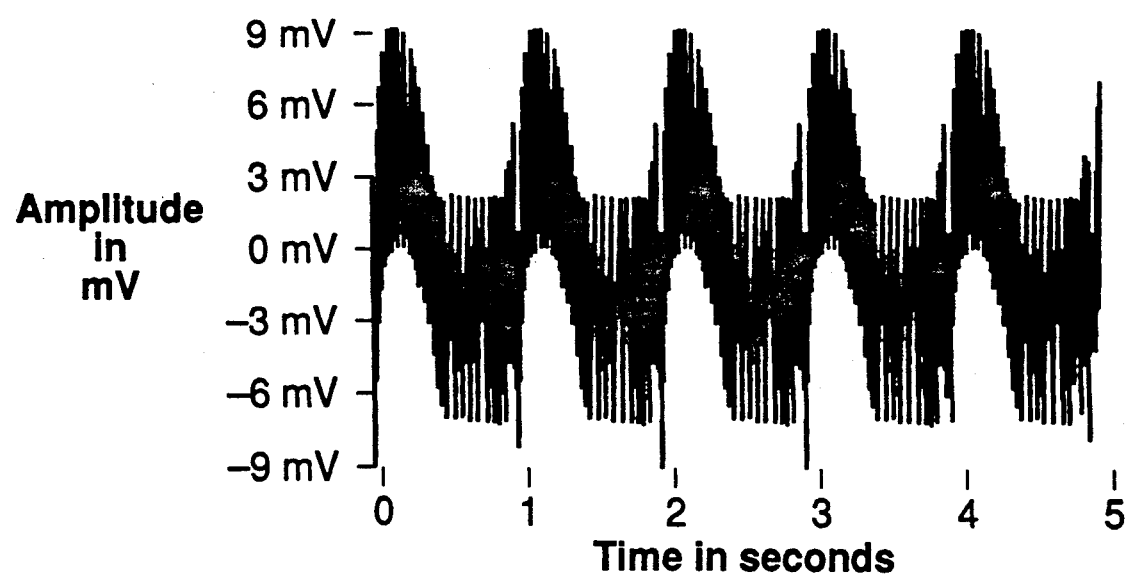
Figure 6C:
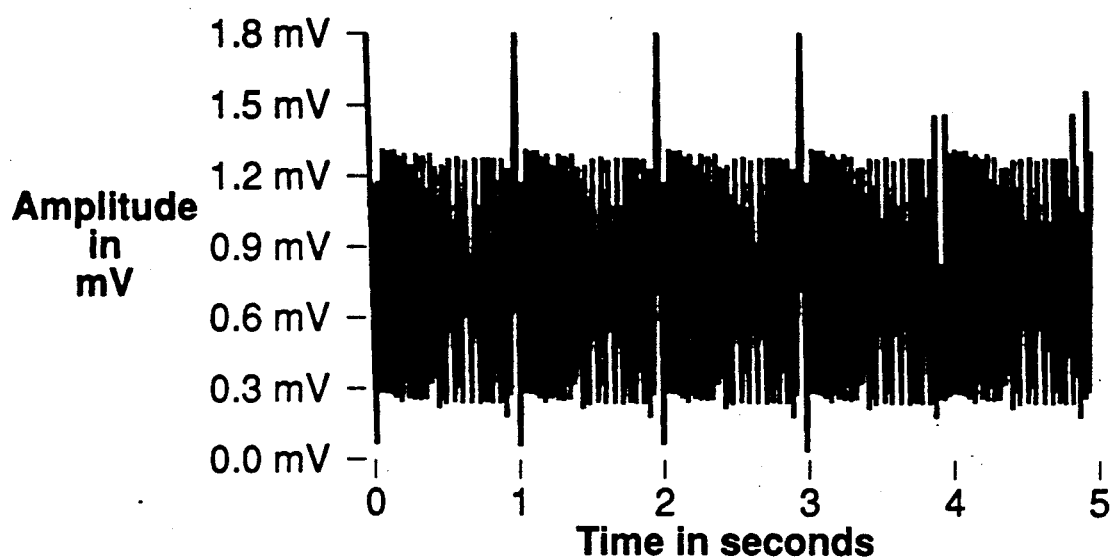
Figure 6D:
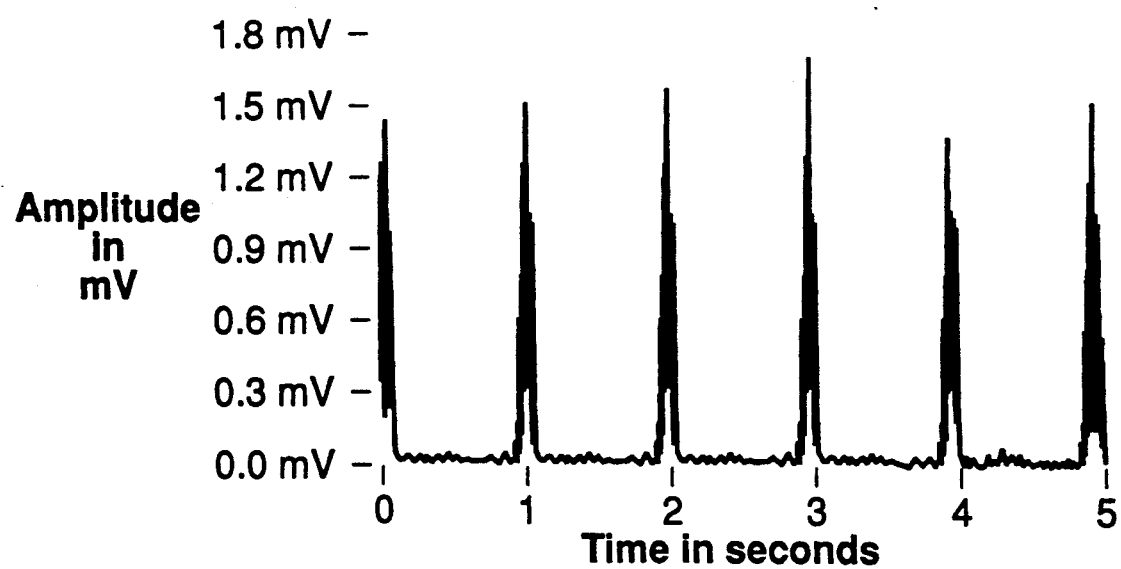

The highpass notch filter 71 may also perform a series of operations to improve cardiac event sensing when the electrical signal manifesting the vent is obscured by continuous line frequency noise. When a control code from the noise rejection controller 70 activates this series of operations, the highpass notch filter performs filtering in the previously described manner and compares each resulting filtered sample, y, with a threshold value. This threshold value may be the same as that loaded into the threshold register 48 of FIG. 1. The highpass notch filter then performs a comparison step analogous to that performed by digital comparator 46 of FIG. 1 to determine whether the filtered data sample exceeds the threshold. A filtered data sample which is larger than the threshold triggers the highpass notch filter to send a signal to the noise rejection controller which indicates the presence of a notch-filtered sense event. This notch-filtered sense event has a much better signal to noise ratio than the standard sense signal (SNS) from the digital comparator 46 of FIG. 1, as is illustrated by FIGS. 6A, 6B, 6C, and 6D. FIG. 6A illustrates an input signal from a series of intrinsic cardiac events. FIG. 6B illustrates the same input signal as distorted by additive 50 Hz noise. FIG. 6C depicts the input to the digital comparator 46 of FIG. 1. FIG. 6D shows the filtered waveform (HPDATA of FIG. 3) after processing by the highpass notch filter 71 within the noise rejection system 65.

Referring again to FIG. 3, when the noise rejection controller 70 activates the lowpass notch filter 73, like the highpass filter, it responds by operating on the sampling frequency Fs digital input signal sequence from the delta modulator and bandpass filter circuit 42 of FIG. 1. The lowpass notch filter 73 determines a running sum of the digital input signal sequence by adding M consecutive samples, ending with the current sample. As in the case of the highpass notch filter, M is the number of samples at frequency Fs which occur within the rejection notch sample period Trn of a rejection notch sample frequency Frn.

The following equation designates the lowpass notch filtering operation:

$$y_n = \sum_{i=0}^{M-1} X_{n-i}$$

where x is the input signal to the lowpass notch filter 73 (the output from the delta modulator and bandpass filter circuit 42 of FIG. 1), y is the filtered digital output (LP DATA of FIG. 3) of the lowpass notch filter, n is the current sample in the sequence, and M is the number of samples in the rejection notch period Trn. The lowpass notch filter eliminates all additive signals, including line frequency noise, having frequencies either at line frequency or at an integer multiple thereof and as to which the sample frequency Fs is a harmonic frequency.

Figure 7:
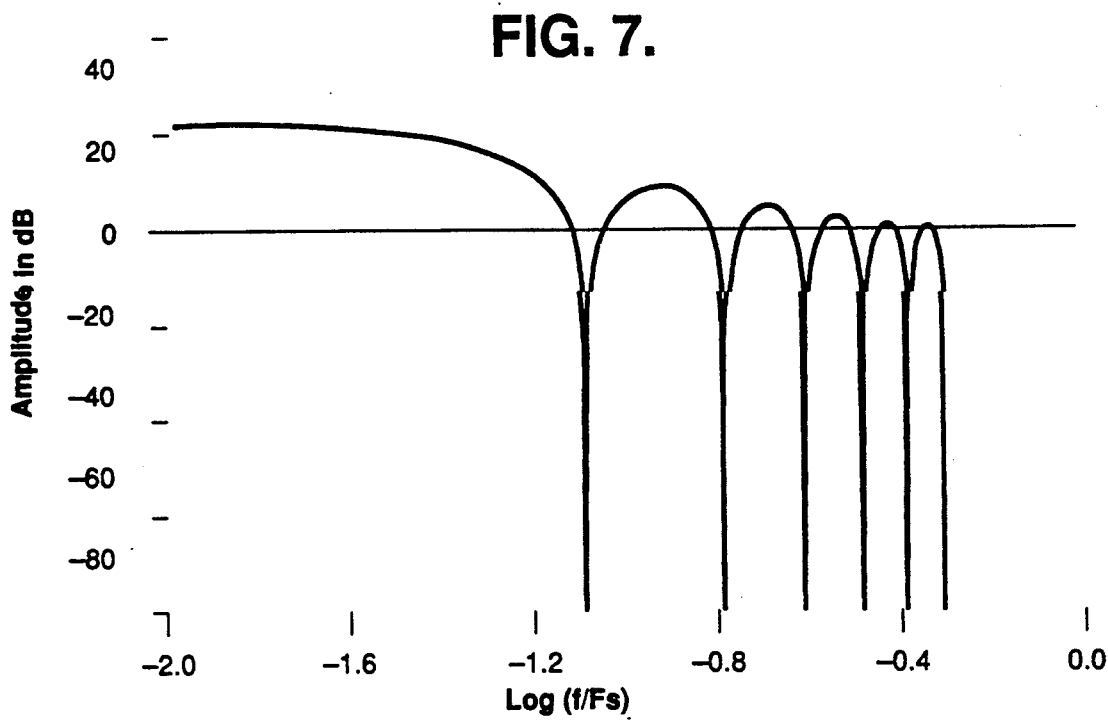
FIG. 7 is a graphical illustration of the bandpass characteristics of a lowpass notch filter employed in the illustrative embodiment of the invention.

FIG. 7 illustrates the frequency response of a lowpass notch filter. In this figure the ordinate scale represents signal amplitude in dB, and the abscissa scale represents the log to the base 10 of the signal frequencies, f, divided by the sampling frequency Fs (600 Hz in this case). As may be seen in the figure, significant attenuation of the signal occurs at points corresponding to 50 Hz and its harmonics.

The noise rejection controller 70 may configure the lowpass notch filter 73 to apply notch filtering for multiple noise frequencies in the same manner and for the same purposes for which multiple frequency highpass notch filtering was selected. The lowpass notch filter 73 again performs the filtering operation at multiple frequencies, compares the outputs y for each sample in the sequence, and selects the minimum value for the overall output. If so configured, the lowpass notch filter 73 may, in the alternative, perform notch filtering for multiple line frequencies, compare the output y to the previous output y for each filtered frequency, and select the output y corresponding to the minimum change from the previous sample for the final lowpass filter output.

Figure 8:
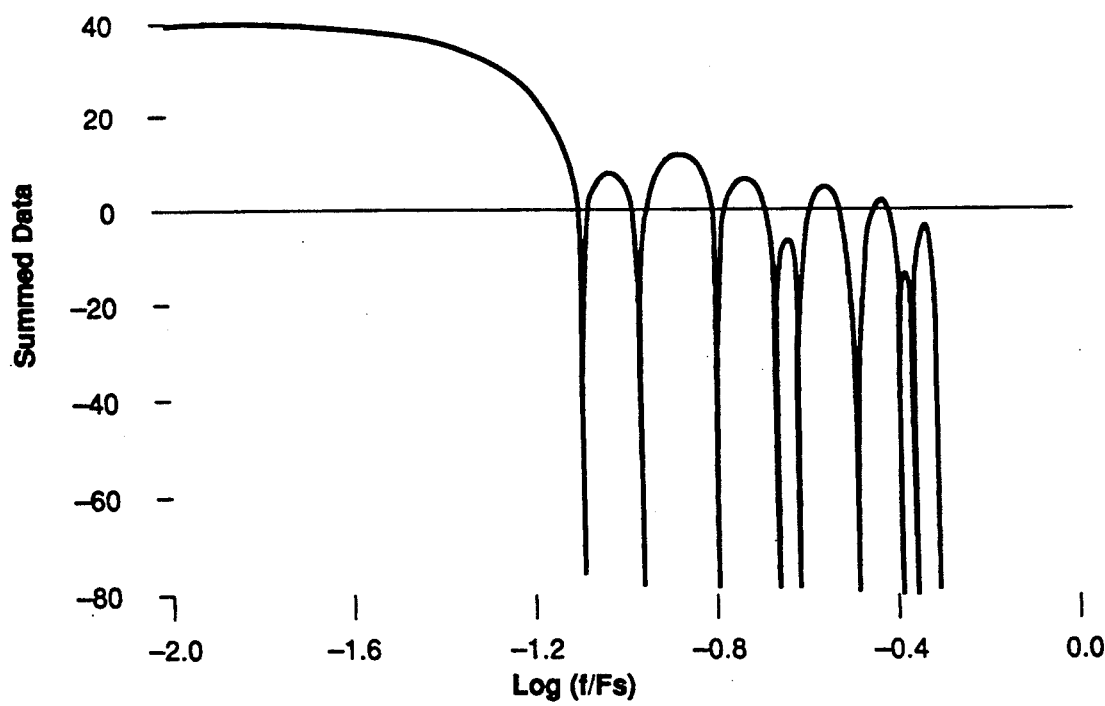
FIG. 8 is a graphical illustration of the bandpass characteristics of a dual frequency 50 Hz and 60 Hz lowpass notch filter employed in the illustrative embodiment of the invention.

FIG. 8 illustrates the frequency response of a 50 Hz and 60 Hz dual frequency lowpass notch filter. In this figure the ordinate scale represents signal amplitude in dB, and the abscissa scale represents the log to the base 10 of the signal frequencies, f, divided by a sampling frequency Fs of 600 Hz. As may be seen in the figure, significant attenuation of the signal occurs at points corresponding to 50 Hz and its harmonics, and also at points corresponding to 60 Hz and its harmonics.

Figure 9A:
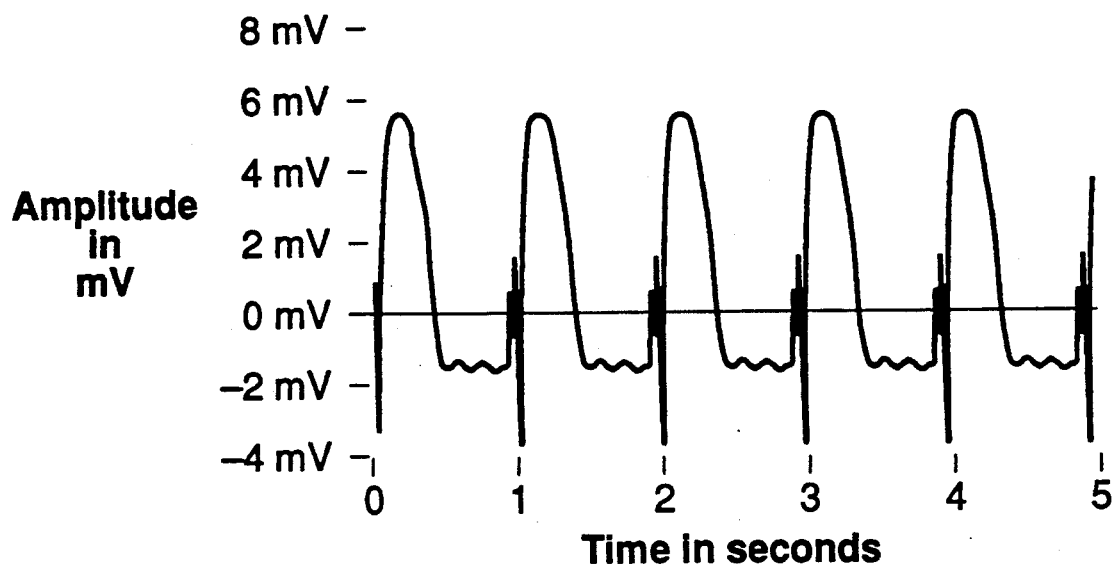
FIGS. 9A, 9B, 9C, and 9D are sample illustrations of cardiac signals at different stages of processing by the dual frequency lowpass filter employed in the illustrative embodiment of the invention.
Figure 9B:
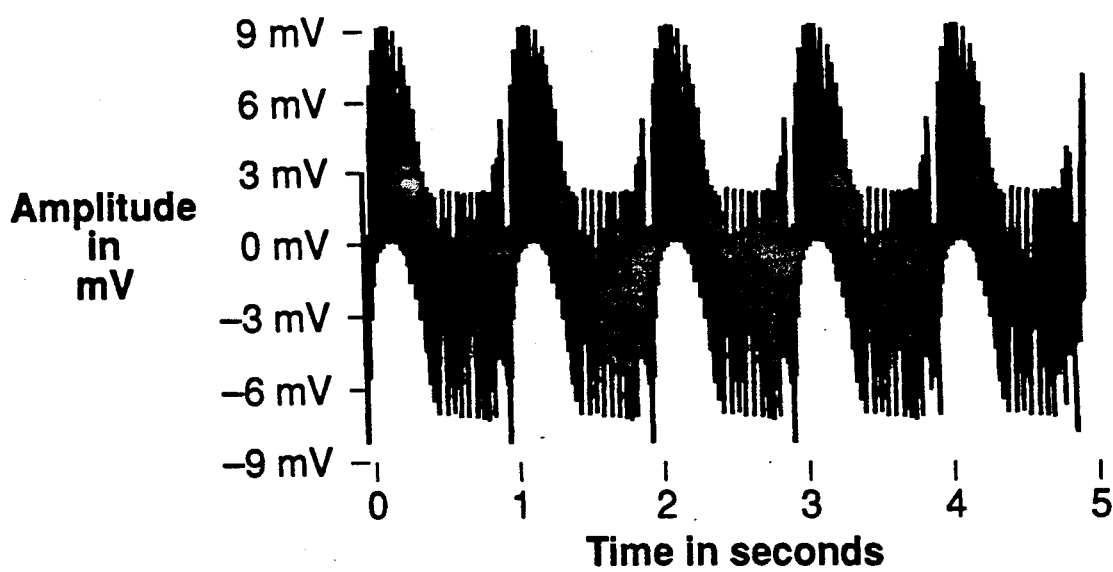
Figure 9C:
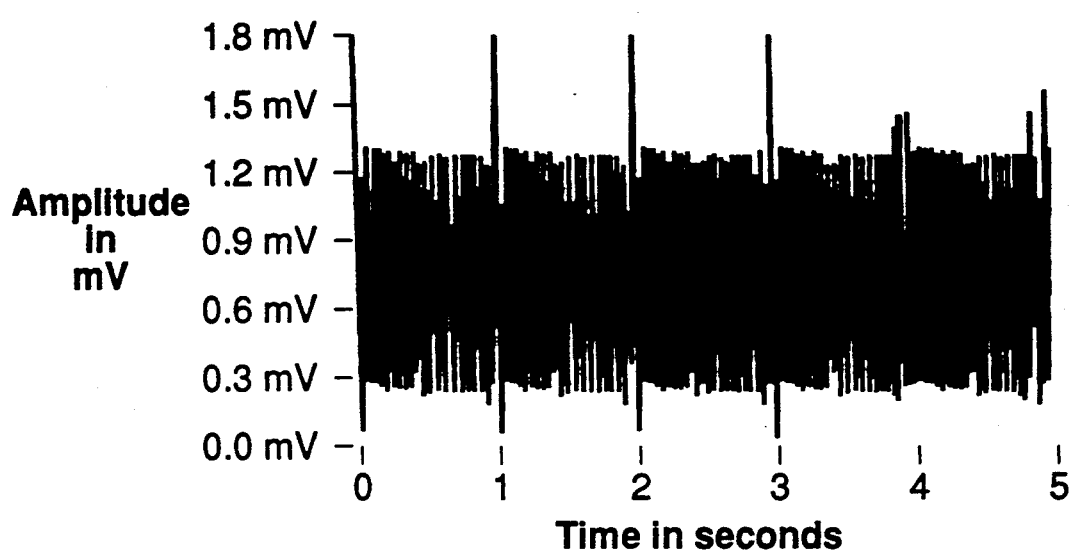
Figure 9D:
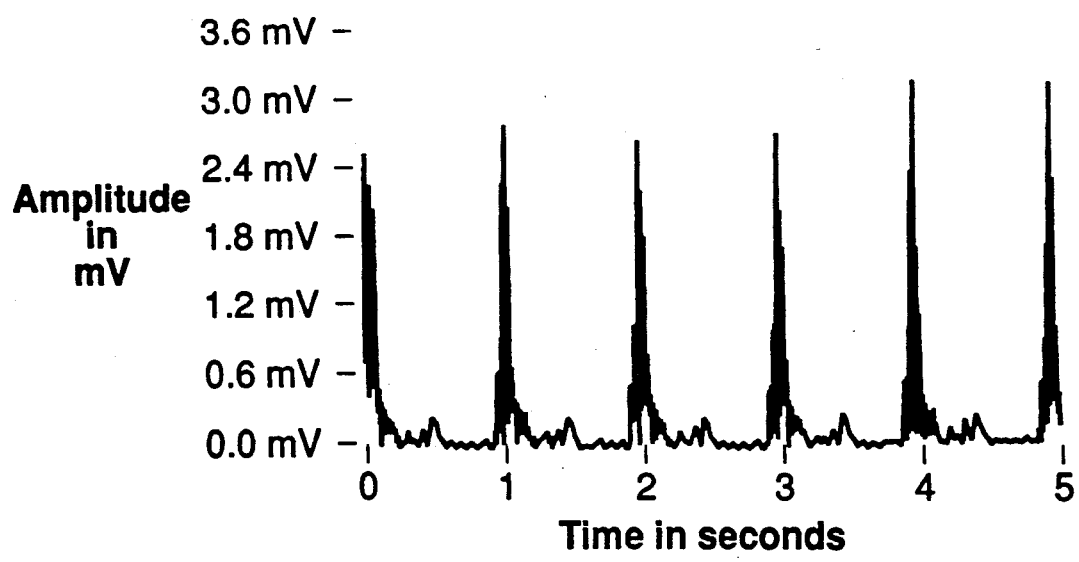

The noise rejection controller 70 may also enable the lowpass notch filter 73 to perform a series of operations, in a similar manner to the operations of the highpass notch filter 71, to improve cardiac event sensing under conditions of high levels of line frequency noise. When enabled, the lowpass notch filter filters the sample sequence, compares each filtered sample to a threshold value, and, if the filtered sample value is larger than the threshold, sends a signal to the noise rejection controller to indicate the presence of a notch-filtered sense event. The lowpass notch-filtered sense event has a much better signal to noise ratio than the standard sense signal (SNS) from the digital comparator 46 of FIG. 1, as is illustrated by FIGS. 9A, 9B, 9C, and 9D. FIG. 9A illustrates an input signal from a series of intrinsic cardiac events. FIG. 9B illustrates the same input signal as distorted by additive 50 Hz noise. FIG. 9C depicts the input to the digital comparator 46 of FIG. 1. FIG. 9D shows the filtered waveform (LP DATA of FIG. 3) after processing by the lowpass notch filter 73 within the noise rejection system 65. While lowpass notch filtering provides improvement in signal to noise ratio in comparison to unfiltered signals, highpass notch filtering produces a greater improvement. Lowpass notch filtering provides less improvement in signal to noise ratio because lowpass filtering inherently smooths the short periods of large changes in the cardiac signal waveform.

The burst processor 72 of FIG. 3, which operates under the control of activating commands from the noise rejection controller 70, distinguishes cardiac signals from bursts of line frequency noise during episodes of amplitude modulated or pulsed EMI. Due to energy consumption considerations in an implantable device, the noise rejection controller activates one of the digital notch filters only after receiving a signal from the digital comparator 46 (FIG. 1), which designates the occurrence of a sensed signal (SNS), and after waiting a predetermined delay interval (for example, 20 to 40 msec). The noise rejection controller may activate either the highpass or lowpass notch filter, but the highpass notch filter is preferred due to the aforementioned improvement in signal to noise ratio.

The burst processor 72 operates on two input data sequences, the output from the delta modulator and bandpass filter block 42 of FIG. 1 and the output from the selected notch filter, 71 or 73. The burst processor takes the absolute value and integrates the notch-filtered sequence for a predetermined interval (for example, 30 msec). The burst processor performs the same absolute value and integration operations on the unfiltered sequence as it does on the notch-filtered sequence, for unfiltered sequence samples which correspond in synchrony with the filtered sequence samples. At the end of the integration period, the burst processor 72 compares the value of the unfiltered sequence integral to the filtered sequence integral. If a burst of noise led to activation of the digital comparator 46 (FIG. 1), the notch filter should cancel the noise frequency components of the input signal. Therefore, for line frequency noise sensing, the integral of the absolute values of the notch-filtered sequence should be very small, theoretically zero, in comparison with the integral of the absolute values of the unfiltered sequence. On the other hand, if a cardiac event such as a QRS complex is also present, the notch filter should not reduce the signal component from the event. In this case, the integral of the absolute values of the filtered sequence should be enhanced by the filtering operation.

In practice, the burst processor classifies a signal as line frequency noise sensing when the filtered integral is smaller than a predetermined fraction of the unfiltered integral (for example, ⅓). In addition, to avoid an incorrect sensing classification of narrow QRS complexes (or very late sensed normal QRS complexes) which may have very little signal amplitude during the classification window following a SNS event, the noise rejection system 65 imposes another condition for classifying a sensed signal as a line frequency noise sense. The absolute value of the maximum input signal during the classification window must be larger than a predetermined percentage of the aforementioned sensing threshold (for example, one half) when the sensed event occurs for classification as a line frequency noise sense. This condition may cause narrow noise impulses to be classified as QRS senses.

FIGS. 10A, 10B, and 10C are sample illustrations of a simulated cardiac signal waveform (FIG. 10A) and associated waveforms (FIGS. 10B and 10C) generated during processing of the cardiac signal waveform in the noise rejection system 65 of the invention. FIGS. 11A, 11B, and 11C are illustrations of a stimulated burst line noise waveform (FIG. 11A) and its associated waveforms (FIGS. 11B and 11C) generated during processing of the burst line noise waveform in the noise rejection system 65. The time scale of both sets of illustrations correspond identically. The amplitudes of the illustrations do not correspond.

One manner for characterizing the ability of cardiac control devices to sense cardiac signals despite additive distortion from amplitude modulated or pulse EMI noise is to measure the response of the sensing circuit to an applied simulated (triangular) cardiac signal (FIG. 10A) and an applied burst of 50 Hz line frequency noise (FIG. 11A). By varying the amplitude of the two input signal waveforms and determining the amplitude which invokes a sense response, it is possible to determine the signal to noise (S/N) ratio which characterizes the sensing circuit. No present-day devices achieve a S/N ratio over 0.9.

FIG. 10B illustrates a simulated cardiac signal waveform which is sensed by a typical cardiac pacemaker sensing circuit. FIG. 11B depicts a burst of line frequency noise which is sensed by the sensing circuit of a typical cardiac pacemaker. The entire waveforms in FIGS. 10B and 11B, including both shaded and unshaded portions, illustrate cardiac signal amplitudes which are acquired using a sensing circuit of a typical cardiac pacemaker. The shaded portions (A) of FIGS. 10B and 11B depict the portions of the waveforms which are analyzed, in a manner to be described in detail hereinafter, to determine whether the incoming signal represents cardiac activity or noise. Normally, a typical pacemaker operating in inhibit mode (VVI) will appropriately detect the single cardiac event of FIG. 10B and inhibit the delivery of a pacing stimulus. The same sensing circuit may cause the pacemaker to incorrectly respond to the noise signal by inhibiting a pacing pulse. Recall that no present-day pacemakers achieve a signal to noise ratio over 0.9. This means that these pacemakers are more likely to inhibit a pacing pulse in response to noise than they are in response to a true cardiac signal. In addition to a poor signal to noise performance, the waveforms of FIGS. 10B and 11B, typify the marked temporal alteration in the output signal which is caused by sensing circuitry filtering.

FIGS. 10C and 11C illustrate the improvements provided by the two operations of highpass notch filtering and output limiting. Output limiting is the operation of comparing the amplitude of the highpass notch filter output to the amplitude of the filter input and setting the output to the lesser of the two amplitudes. FIGS. 10C and 11C are the results of highpass notch filtering and output limiting in response to the sensing of the cardiac signal of FIG. 10A and the noise burst of FIG. 11A, respectively. The entire waveforms in FIGS. 10C and 11C, including both shaded and unshaded portions, illustrate the result after applying highpass notch filtering but before applying output limiting to the sensed waveforms of FIGS. 10B and 11B. Recall that the noise rejection controller 70 (FIG. 3) waits a predetermined delay interval between triggering upon a sensed signal and beginning the notch filter operation. Inherently, due to the time required to fill the data buffer for the notch frequency filters with valid data, this produces an effective blanking period following the comparator sense detect. Common durations for this blanking interval range from about 20 to 50 ms. The initial unshaded portions of FIGS. 10C and 11C result from this blanking interval. These initial unshaded portions of FIGS. 10C and 11C correspond in time to the initial unshaded portions of FIGS. 10B and 11B. (The initial unshaded portions of FIGS. 10C and 11C cannot be analyzed due to this inherent blanking period and the waveforms of FIGS. 10C and 11C are analyzed in comparison with the waveforms of FIGS. 10B and 11B. Therefore, comparative analysis of the waveforms, to be consistent, does not include the initial portions of FIGS. 10B and 11B.) The shaded portions of FIGS. 10C and 11C depict the further result after applying output limiting to the highpass filtered waveforms. To perform output limiting, the burst processor 72 of FIG. 3 limits the value of each filter output sequence element to be no greater than the corresponding input sequence element. This reduces the filter output following a sudden termination of a noise burst and reduces the notch filter output in response to the rapid termination of the noise burst. Thus, the burst processor 72 sets the value of each output sequence element not only to the minimum absolute value for each notch filtered component (for example, a 50 Hz and a 60 Hz notch filter), but also to the minimum with respect to the absolute value of the input sequence element. The highpass notch filter in this example is a dual frequency filter which removes 50 Hz and 60 Hz line noise.

The shaded portions (B) of the waveforms in FIGS. 10C and 11C illustrate the signal amplitudes which the sensing circuit, containing the highpass notch filtering and output limiting of the present invention, will detect. Thus, when a natural cardiac electrical event (FIG. 10A) triggers a hardware sense detect signal from the digital comparator 46 (FIG. 1), the system of the present invention acquires a sensed cardiac electrical waveform (FIG. 10B), then integrates parts of the signal for analysis (the shaded portion A of FIG. 10B). The system then performs highpass filtering, including an inherent blanking period, and output limiting (FIG. 10C), then integrates a portion of the processed signal (the shaded portion B of FIG. 10C) corresponding in time to the integrated portion of the unprocessed signal. The system compares the unfiltered (A) integral to the filtered (B) integral. Because the filtered integral (B) is not smaller than a predetermined fraction of the unfiltered integral (A), the event is classified as a natural heart QRS signal. When a burst of noise (FIG. 11A) triggers a hardware sense signal, the system obtains a sensed noise waveform (FIG. 11B), and integrates part of the signal (the shaded portion A of FIG. 11B). The system performs highpass filtering with blanking and output limiting (FIG. 11C), and integrates a portion of the filtered signal (the shaded portion B of FIG. 11C). When the system compares the unfiltered signal (A) integral to the filtered (B) integral, the filtered (B) integral is much smaller. Therefore, the system classifies the event as noise. Thus, for a sudden onset of noise, a sense detect is correctly classified as a noise event, thereby improving the signal to noise ratio of the system. According to computer simulations, the signal to noise test ratio of the noise rejection system of the present invention improves to a value greater than 10, as contrasted to the 0.9 signal to noise ratio prevalent in prior art pacemakers.

The noise rejection system of the invention provides a high level of continuous and burst line frequency noise rejection that is useful in cardiac control devices, including bradycardia and tachycardia therapy devices. Improved reliability sensing allows additional signal processing and analysis for advanced arrhythmia detection methods which depend on accurate sensing of true spontaneous atrial and ventricular electrical events. Furthermore, the system effectively reduces noise in cardiac monitoring devices, encompassing implantable and surface Holter monitors and electrophysiology recording devices.

Thus, a noise rejection system in a cardiac control and monitoring device has been shown and described which accomplishes substantial improvement in distinguishing cardiac electrical signals from continuous and burst line frequency noise.

Although the invention has been described with reference to a particular embodiment, it is to be understood that this embodiment is merely illustrative of the application of the principles of the invention. Hence numerous modifications may be made therein and other arrangements may be devised without departing from the spirit and scope of the invention.

What is claimed is:

1. A physiological event signal sensing system in a cardiac medical device, comprising:
   means for sensing a cardiac signal, said cardiac signal including a physiological component and including a noise component which is produced by power line interference;
   means for sampling the instantaneous amplitude values of said cardiac signal at a sampling frequency of Fs;
   means for combining said amplitude values for n consecutive samples to derive a notch filter output signal retaining said physiological component while attenuating said power line noise component, wherein n is preselected so that Fs/n defines the frequency of the power line noise component and wherein said amplitude values are combined according to a predetermined notch filter function;
   means for comparing said notch filter output signal with a predetermined threshold level; and, means responsive to said notch filter output signal exceeding the predetermined threshold level for determining the occurrence of a heartbeat.

2. A physiological event signal sensing system in accordance with claim 1, wherein said notch filter function designates a highpass filter function in which the nth previous sample of said instantaneous amplitude values of said cardiac signal is subtracted from the current sample.

3. A physiological event signal sensing system in accordance with claim 1, wherein said notch filter function designates a lowpass filter function in which n consecutive samples of said instantaneous amplitude values of said cardiac signal are summed.

4. A physiological event signal sensing system in accordance with claim 1, wherein said power line component frequency, Fs/n, is 60 Hz.

5. A physiological event signal sensing system in accordance with claim 1, wherein said power line component frequency, Fs/n, is 50 Hz.

6. A physiological event signal sensing system in accordance with claim 1, wherein said combining means includes multiple associated notch filter elements, each of said notch filter elements serving to attenuate a different power line frequency component Fs/n and each of said notch filter element including a separate sample count n and a separate predetermined notch filter function.

7. A physiological event signal sensing system in accordance with claim 6, wherein said notch filter function designates a highpass filter function in which the nth previous sample of said instantaneous amplitude values of said cardiac signal is subtracted from the current sample.

8. A physiological event signal sensing system in accordance with claim 6, wherein said notch filter function designates a lowpass filter function in which n consecutive samples of said instantaneous amplitude values of said cardiac signal are summed.

9. A physiological event signal sensing system in accordance with claim 6, wherein one said power line component frequency, Fs/n1, is 60 Hz and another said power line component frequency, Fs/n2, is 50 Hz.

10. A physiological event signal sensing system in accordance with claim 6, wherein said combining means further comprises:
means for comparing each output signal sequence sample from each of said multiple associated notch filter elements to a time corresponding output signal sequence sample from another of said multiple associated notch filter elements, and
means for setting the value of each sample of said notch filter output signal sequence to the smallest of said time corresponding output signal sequence samples.

11. A physiological event signal sensing system in accordance with claim 6, wherein said combining means further comprises:
means for subtracting the previous time sample of said notch filter output signal sequence from a current time sample of the output signal sequence for each of said multiple associated notch filter elements to determine a delta change signal sample for each of said multiple associated notch filters,
means responsive to said subtracting means for comparing said delta change signal sample for each of said multiple associated notch filter elements to said delta change signal samples from all other of said multiple associated notch filter elements, and
means for setting the value of each sample of said notch filter output signal sequence to the output signal sequence sample associated with the notch filter element with the smallest delta change signal sample.

12. A physiological event signal sensing system in accordance with claim 1, further comprising:
means for disabling said cardiac signal sampling means,
means for comparing said sensed cardiac signal to a preliminary predetermined threshold level, and
means responsive to said sensed cardiac signal exceeding the preliminary predetermined threshold level for activating said cardiac signal sampling means.

13. A physiological event signal sensing system in a cardiac medical device, comprising:
means for sensing a cardiac signal, said cardiac signal including a physiological component and including a noise component which is produced by power line interference;
means for sampling the instantaneous amplitude values of said cardiac signal at a sampling frequency of Fs;
means for combining said amplitude values for n consecutive samples to derive a notch filter output signal retaining said physiological component while attenuating said power line noise component, wherein n is preselected so that Fs/n defines the frequency of the power line noise component and wherein said amplitude values are combined according to a predetermined notch filter function;
rectifying means responsive to said sampling means for rectifying said sampled cardiac signal and responsive to said combining means for rectifying said notch filter output signal;
means for comparing each of said rectified notch filter output signal samples to the corresponding time sample of said rectified sampled cardiac signal to determine the sample having a smaller value in each pair of compared corresponding time samples;
means responsive to said comparing means for setting each sample of said notch filter output signal to said smaller value to provide a minimized notch filter output signal;
means for comparing said minimized notch filter output signal with a predetermined threshold level; and,
means responsive to said notch filter output signal exceeding the predetermined threshold level for determining the occurrence of a heartbeat.

14. A physiological event signal sensing system in accordance with claim 13, further comprising:
means for disabling said cardiac signal sampling means,
means for comparing said sensed cardiac signal to a preliminary predetermined threshold level, and
means responsive to said sensed cardiac signal exceeding the preliminary predetermined threshold level for activating said cardiac signal sampling means.

15. A physiological event signal sensing system in accordance with claim 14, further comprising:
means for delaying said activation of said cardiac signal sampling means for an interval of a predetermined duration following said sensed cardiac signal exceeding the preliminary predetermined threshold level; and means for waiting an interval of a second predetermined duration before disabling said cardiac signal sampling means.

16. A physiological event signal sensing system in accordance with claim 13, wherein said notch filter function designates a highpass filter function in which the nth previous sample of said instantaneous amplitude values of said cardiac signal is subtracted from the current sample.

17. A physiological event signal sensing system in accordance with claim 13, wherein said notch filter function designates a lowpass filter function in which n consecutive samples of said instantaneous amplitude values of said cardiac signal are summed.

18. A physiological event signal sensing system in accordance with claim 13, wherein said power line component frequency, Fs/n, is 60 Hz.

19. A physiological event signal sensing system in accordance with claim 13, wherein said power line component frequency, Fs/n, is 50 Hz.

20. A physiological event signal sensing system in accordance with claim 13, wherein said combining means includes multiple associated notch filter elements, each of said notch filter elements serving to attenuate a different power line frequency component Fs/n and each of said notch filter elements including a separate sample count n and a separate predetermined notch filter function.

21. A physiological event signal sensing system in accordance with claim 20, wherein said notch filter function designates a highpass filter function in which the nth previous sample of said instantaneous amplitude values of said cardiac signal is subtracted from the current sample.

22. A physiological event signal sensing system in accordance with claim 20, wherein said notch filter function designates a lowpass filter function in which n consecutive samples of said instantaneous amplitude values of said cardiac signal are summed.

23. A physiological event signal sensing system in accordance with claim 20, wherein one said power line component frequency, Fs/n1, is 60 Hz and another said power line component frequency, Fs/n2, is 50 Hz.

24. A physiological event signal sensing system in accordance with claim 20, wherein said combining means further comprises:

means for comparing each output signal sequence sample from each of said multiple associated notch filter elements to a time corresponding output signal sequence sample from another of said multiple associated notch filter element, and means for setting the value of each sample of said notch filter output signal sequence to the smallest of said time corresponding output signal sequence samples.

25. A physiological event signal sensing system in accordance with claim 20, wherein said combining means further comprises:

means for subtracting the previous time sample of said notch filter output signal sequence from a current time sample of the output signal sequence for each of said multiple associated notch filter elements to determine a delta change signal sample for each of said multiple associated notch filters, means responsive to said subtracting means for comparing said delta change signal sample for each of said multiple associated notch filter elements to said delta change signal samples from all other of said multiple associated notch filter elements, and means for setting the value of each sample of said notch filter output signal sequence to the output signal sequence sample associated with the notch filter element with the smallest delta change signal sample.

26. A physiological event signal sensing system in a cardiac medical device, comprising:

means for sensing a cardiac signal, said cardiac signal including a physiological component and including a noise component which is produced by power line interference;

means for sampling the instantaneous amplitude values of said cardiac signal at a sampling frequency of Fs;

means for combining said amplitude values for n consecutive samples to derive a notch filter output signal retaining said physiological component while attenuating said power line noise component, wherein n is preselected so that Fs/n defines the frequency of the power line noise component and wherein said amplitude values are combined according to a predetermined notch filter function;

integrating means responsive to said sampling means for integrating said sampled cardiac signal and responsive to said combining means for integrating said notch filter output signal;

means for determining the ratio of said integrated notch filter output signal to said integrated sampled cardiac signal, means for comparing said ratio with a predetermined threshold level; and means responsive to said notch filter output signal exceeding the threshold level for determining the occurrence of a heartbeat.

27. A method of operating a physiological event signal sensing system in a cardiac medical device, comprising the steps of:

sensing a cardiac signal, said cardiac signal including a physiological component and including a noise component which is produced by power line interference;

sampling the instantaneous amplitude values of said cardiac signal at a sampling frequency of Fs;

combining said amplitude values for n consecutive samples to derive a notch filter output signal retaining said physiological component while attenuating said power line noise component, wherein n is preselected so that Fs/n defines the frequency of the power line noise component and wherein said amplitude values are combined according to a predetermined notch filter function;

comparing said notch filter output signal with a predetermined threshold level; and, determining the occurrence of a heartbeat when said notch filter output signal exceeds a predetermined threshold level.

28. A method of operating a physiological event signal sensing system in a cardiac medical device, comprising the steps of:

sensing a cardiac signal, said cardiac signal including a physiological component and including a noise component which is produced by power line interference;

sampling the instantaneous amplitude values of said cardiac signal at a sampling frequency of Fs;

combining said amplitude values for n consecutive samples to derive a notch filter output signal retaining said physiological component while attenuating said power line noise component, wherein n is preselected so that Fs/n defines the frequency of the power line noise component and wherein said amplitude values are combined according to a predetermined notch filter function;

rectifying said sampled cardiac signal;

rectifying said notch filter output signal;

comparing each of said rectified notch filter output signal samples to the corresponding time sample of said rectified sampled cardiac signal to determine the sample having a smaller value in each pair of compared corresponding time samples;

setting each sample of said notch filter output signal to the smaller value resulting from said comparing step to provide a minimized notch filter output signal;

comparing said minimized notch filter output signal with a predetermined threshold level; and, determining the occurrence of a heartbeat when said minimized notch filter output signal exceeds a predetermined threshold level.

* * * * *